(12) United States Patent
Maheshwari

(10) Patent No.: US 11,447,787 B2
(45) Date of Patent: Sep. 20, 2022

(54) GENERATION OF HAPLOID PLANTS

(71) Applicant: The Regents of the University of California, Oakland, CA (US)

(72) Inventor: Arundhati Maheshwari, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 269 days.

(21) Appl. No.: 16/500,705

(22) PCT Filed: Mar. 29, 2018

(86) PCT No.: PCT/US2018/025254
§ 371 (c)(1),
(2) Date: Oct. 3, 2019

(87) PCT Pub. No.: WO2018/191032
PCT Pub. Date: Oct. 18, 2018

(65) Prior Publication Data
US 2020/0224210 A1   Jul. 16, 2020

Related U.S. Application Data

(60) Provisional application No. 62/483,750, filed on Apr. 10, 2017.

(51) Int. Cl.
*C12N 15/82* (2006.01)
(52) U.S. Cl.
CPC ..... *C12N 15/8231* (2013.01); *C12N 15/8233* (2013.01)
(58) Field of Classification Search
CPC ................. C12N 15/8231; C12N 15/8233
See application file for complete search history.

(56) References Cited

U.S. PATENT DOCUMENTS

| | | | |
|---|---|---|---|
| 5,749,169 | A | 5/1998 | Briggs et al. |
| 8,618,354 | B2 | 12/2013 | Chan et al. |
| 10,912,264 | B2 | 2/2021 | Chan et al. |
| 2009/0144849 | A1 | 6/2009 | Lutfiyya |
| 2010/0017908 | A1 | 1/2010 | Zhao et al. |
| 2015/0247157 | A1 | 9/2015 | Chamberlin et al. |
| 2017/0009242 | A1 | 1/2017 | McKinley et al. |

FOREIGN PATENT DOCUMENTS

| | | |
|---|---|---|
| WO | 2010/079432 A1 | 7/2010 |
| WO | 2012/075195 A1 | 6/2012 |

OTHER PUBLICATIONS

Ravi, M. et al., (Oct. 2010) Genetics vol. 186; pp. 461-471. (Year: 2010).*
Cordova, A., Honors Thesis (May 2015) of Stanford University, 29 pages. (Year: 2015).*
Extended European Search Report in EP Application 18785186.0 dated Dec. 4, 2020; 7 pages.
Faden, F. et al.; "Generic tools for conditionally altering protein abundance and phenotypes on demand"; *Biological Chemistry*; vol. 395, No. 7-8; 2014; pp. 737-762.
Smirnova, O.G. et al.; "Simple database to select promoters for plant transgenesis"; *Transgenic Research*: Kluwer Academic Publishers-Plenum Publishers, NE; vol. 21, No. 2; Aug. 3, 2011; pp. 429-437.
International Search Report and Written Opinion in PCT/US2018/025254 dated Jul. 23, 2018; 13 pages.
Collins, K.A. et al.; "Proteolysis Contributes to the Exclusive Centromere Localization of the Yeast Cse4/CENP-A Histone H3 Variant"; *Current Biology*: vol. 14, Issue 21; Nov. 9, 2004; pp. 1968-1972.
Cordova, A.; "Rapid, inducible degradation of CENP-C suggests novel roles for CENP-C in centromere assembly and maintenance"; *Thesis*; Stanford University, Department of Biology; Jun. 14, 2015; pp. 1-29.
Hoffmann, S et al.; "CENP-A Is Dispensable for Mitotic Centromere Function after Initial Centromere/Kinetochore Assembly"; *Cell Reports*: vol. 17, Issue 9; Nov. 22, 2016; pp. 2394-2404.
Taxis, C. et al.; "Efficient protein depletion by genetically controlled deprotection of a dormant N-degron"; *Molecular Systems Biology*: vol. 5, No. 267; Apr. 28, 2009; pp. 1-7.
Wood, L.; "Auxin/AID Versus Conventional Knockouts: Distinguishing the Roles of CENP-T/W in Mitotic Kinetochore Assembly and Stability"; *Open Biology*; vol. 6, Issue 1; Jan. 1, 2016; pp. 1-16.
Supplementary European Search Report from EP 10822533.5, dated Aug. 20, 2013.
The International Search Report from PCT/2010/051483, dated Jan. 6, 2011.
Maheshwari, S. et al.; "Naturally Occurring Differences in CENH3 Affect Chromosome Segregation in Zygotic Mitosis of Hybrids"; *PLOS Genetics*; vol. 11, No. 2; Jan. 26, 2015; pp. 1-20.
Black et al.; "Structural determinants for generating centromeric chromatin" Nature; 430:578-582 (2004).
Chen et al.; "The N Terminus of the centromere H3-like protein Cse4p performs an essential function distinct from that of the histone fold domain"; Mol. Cell Biol.; 20(18):7037-7048 (2000).
d'erfurth et al.; "Turning Meiosis into Mitosis"; PLoS Biol.; Jun. 2009; 7(6): e1000124 (10 pages) ePub Jun. 9, 2009. doi: 10.1371/journal.pbio.1000124.
Forster et al.; "The resurgence of haploids in higher plants"; Trends in Plant Sci.; 12(8):368-375 (2007).
Keith, et al.; "Analysis of Primary Structural Determinants That Distinguish the Centromere-Specific Function of Histone Variant Cse4p from Histone H3"; *Mol. Cell. Biol.*; 19 (9); 6130-6139 (Sep. 1999).
Konev et al.; "The CHD1 motor protein is required for depositoin of histone variant H3.3 into chromatin in vivo"; Science; 317(5841):1087-1090 (2007).
Lermontova, Inna et al.; "Loading of Arabidopsis Centromeric Histone CENH3 Occurs Mainly during G2 and Requires the Presence of the Histone Fold Domain" 2006, The Plant Cell, vol. 18, pp. 2443-2451.
Li, Xuexian et al.; "Fused sister kinetochores initiate the reductional division in meiosis I"; 2009, Nature Cell Biology, vol. 11, pp. 1103-1108.

(Continued)

*Primary Examiner* — Russell Kallis
(74) *Attorney, Agent, or Firm* — Kilpatrick Townsend and Stockton LLP

(57) ABSTRACT

Methods of making haploid plants.

13 Claims, No Drawings

Specification includes a Sequence Listing.

(56) References Cited

OTHER PUBLICATIONS

Marimuthu et al., "Synthetic Clonal Reproduction Through Seeds"; 2011, Science; vol. 331, pp. 876.
Nagaki, Kiyotaka et al.; "Sequencing of a rice centromere uncovers active genes"; 2004, Nature Genetics, vol. 36, No. 2, pp. 138-145.
Ravi et al.; "Haploid plants produced by centromere-mediated genome elimination"; Nature; 464(7288):615-620 (Mar. 2010).
Ravi et al.; "The rapidly evolving centromere-specific histone has stringent functional requirements in *Arabidopsis thaliana*"; Genetics; 186(2):461-471 (Oct. 2010). ePub Jul. 13, 2010.
Régnier et al.; "CENP-A is required for accurate chromosome segregation and sustained kinetochore association of BubR1"; Mol. Cell Biol.; 25(10):3967-3981 (2005).
Strepp et al. "Plant nuclear gene knockout reveals a role in plastid division for the homolog of the bacterial cell division protein FtsZ, an ancestral tubulin"; Proc. Natl. Acad. Sci. USA; 95:4368-4373 (1998).
Uniprot reference: A4PIF4_LEPVR, May 15, 2007; retrieved from the internet <URL: http://www.genome.jp/dbget-bin/www_bget?uniprot:A4PIF4_LEPVR>, Seq ID No. 436, 1 page.
Wang, et al.; "Characterization of CENH3 proteins and centromere-associated DNA sequences in diploi and allotetraploid *Brassica species*"; Chromosoma, (2011), 120: pp. 353-365.
Yu, HengXiu et al.; "Generating of rice OsCENH3-GFP transgenic plants and their genetic applications"; 2008, Chinese Science Bulletin, vol. 53, No. 19, pp. 2981-2988.
Marimuthu, M.P.A. et al.; "Epigenetically mismatched parental centromeres trigger genome elimination in hybrids"; Sci. Adv.; vol. 7; Nov. 19, 2021; 18 pages.
Wang, N. et al.; "Hapoid induction by a maize *cenh3* null mutant"; Sci. Adv.; vol. 7; Jan. 20, 2021; 7 pages.

\* cited by examiner

GENERATION OF HAPLOID PLANTS

CROSS-REFERENCE TO RELATED PATENT APPLICATIONS

The present patent application is a US National Phase Application Under 371 of PCT/US2018/025254 filed Mar. 29, 2018, which claims benefit of priority to U.S. Provisional Patent Application No. 62/483,750, filed Apr. 10, 2017, each of which is incorporated by reference for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 081906-221420US-1152060_SequenceListing.txt, created on Aug. 7, 2019, 63,096 bytes, machine format IBM-PC, MS-Windows operating system, is hereby incorporated by reference in its entirety for all purposes.

BACKGROUND OF THE INVENTION

Typical breeding of diploid plants relies on screening numerous plants to identify novel, desirable characteristics. Large numbers of progeny from crosses often must be grown and evaluated over several years in order to select one or a few plants with a desired combination of traits.

The plant breeding process can be accelerated by producing haploid plants, the chromosomes of which can be doubled using colchicine or other means. Such doubled haploids produce instant homozygous lines in one generation, which is significantly shorter than the approximately 8-10 generations of inbreeding that is typically required for diploid breeding. Thus, methods of producing haploid plants that can be doubled to generate fertile doubled haploids can dramatically improve the efficiency and effectiveness of plant breeding by producing true-breeding (homozygous) lines in only one generation.

BRIEF SUMMARY OF INVENTION

Brief summary: Cell-specific degradation of centromeric proteins, such as CENTROMERIC HISTONE 3 (CENH3), by an inducible N-degron, in order to produce plant gametes with uncompetitive chromosomes that are lost during post-fertilization mitosis, thereby leading to a halving of chromosome number in progeny.

Changes to CENH3, a protein in the complex that marks the centromeres of plant chromosomes, have been shown to produce gametes whose chromosomes are eliminated in crosses with wildtype gametes (Ravi & Chan, 2010). In *Drosophila*, depletion of the homologous CENH3 by protein degradation in sperm cells has also been shown to result in genome elimination upon fertilization with a wildtype egg cell (Raychaudhuri et al., 2012).

Cell- or tissue-specific target protein down-regulation has been achieved by using dormant N-degrons that lead to protein degradation after activation by a specific tobacco etch virus (TEV) protease. Dormant N-degrons were first used as a strategy for targeted protein depletion in yeast by Michael Knop, Christoff Taxis and colleagues at the EMBL in Heidelberg (Taxis et al. 2009). A recent paper from Jan Lohmann's lab at the University of Heidelberg shows that the Taxis et al. method can also be used for targeted degradation of the WUSCHEL protein in Arabidopsis (Daum et al., 2014).

The degron strategy for gamete-specific CenH3 depletion has advantages over strategies that lead to transcriptional or translational repression. For example, the *Arabidopsis* CenH3 is strongly expressed in sperm cells but hard to detect in central and egg cells, suggesting that an egg- and/or central cell-specific RNA interference (RNAi) or RNA-directed DNA methylation (RdDM) approach against CenH3 might not be successful at inducing genome elimination. Also, gamete-specific suppression of transcription or translation may not deplete CenH3 reserves to extent where genome elimination occurs. As strong gamete lineage-specific promoters that are specific to one sex but not the other have yet to be identified, gamete-specific protein depletion is the most feasible strategy at this time.

Provided here is a new strategy for cell- or tissue-specific CENH3 down-regulation: dormant N-degrons that lead to protein degradation after activation by a specific tobacco etch virus (TEV) protease.

Also provided are methods of targeting a kinetochore protein for degradation and generating haploid (or half ploidy of parent plant) progeny. In some embodiments, the methods comprise:

a. introducing into a gamete cell of a parent plant a polypeptide comprising an peptide sequence linked to a protease cleavage site linked to N-degron linked to a kinetochore protein, wherein the peptide sequence is of sufficient length to block the polypeptide in an N-degron-dependent manner, and;

b. introducing into the gamete cell of a parent plant a protease that targets the protease cleavage site, thereby releasing the peptide sequence such that the N-degron is at the amino terminus of the polypeptide, thereby targeting the polypeptide for degradation.

In some embodiments, one or two alleles of the endogenous kinetochore protein coding sequence of the plant is inactivated or knocked out.

In some embodiments, the kinetochore protein is selected from CENH3, CENPC, MIS12, NDC80 or NUF2.

In some embodiments, the protease is a tobacco etch virus (TEV) protease.

In some embodiments, the introducing in step a comprises expressing the polypeptide from an expression cassette comprising a promoter operably linked to a sequence encoding the polypeptide. In some embodiments, the promoter is a kinetochore protein gene promoter.

In some embodiments, the introducing in step b comprises expressing the protease from an expression cassette comprising a heterologous promoter specific for a gamete lineage operably linked to a sequence encoding the protease. In some embodiments, the promoter specific for a gamete lineage is specific for a central cell, egg cell, or sperm cell.

In some embodiments, the methods further comprise generating selfed progeny from the plant and selecting progeny from the plant having half the chromosomes of the plant. In some embodiments, the methods further comprise crossing the plant expressing the polypeptide from steps a and protease from step b to a second parent plant and selecting progeny from the cross having half the chromosomes of the second parent plant. In some embodiments, the selected progeny from selfing or the cross are haploid. In some embodiments, the method further comprises generating doubled haploid plants from the haploid progeny.

Also provided are plants comprising:

a first expression cassette comprising a promoter operably linked to a polynucleotide encoding a polypeptide comprising an peptide sequence linked to a protease cleavage site linked to N-degron linked to a kinetochore protein, wherein the peptide sequence is of sufficient length to block the polypeptide in an N-degron-dependent manner and/or a second expression cassette comprising a heterologous promoter linked to a second polynucleotide encoding the protease, wherein the heterologous promoter is specific for a gamete lineage.

In some embodiments, the promoter specific for a gamete lineage is specific for a central cell, egg cell, or sperm cell.

Also provided is an expression cassette comprising a promoter operably linked to a polynucleotide encoding a polypeptide comprising an peptide sequence linked to a protease cleavage site linked to N-degron linked to a kinetochore protein.

Also provided is an expression cassette comprising a heterologous promoter linked to a second polynucleotide encoding the protease, wherein the heterologous promoter is specific for a gamete lineage. In some embodiments, the promoter specific for a gamete lineage is specific for a central cell, egg cell, or sperm cell.

Definitions

An "endogenous" gene or protein sequence refers to a non-recombinant sequence of an organism as the sequence occurs in the organism before human-induced mutation of the sequence. A "mutated" sequence refers to a human-altered sequence. Examples of human-induced mutation include exposure of an organism to a high dose of chemical, radiological, or insertional mutagen for the purposes of selecting mutants, as well as recombinant alteration of a sequence. Examples of human-induced recombinant alterations can include, e.g., fusions, insertions, deletions, and/or changes to the sequence.

The term "promoter" refers to regions or sequence located upstream and/or downstream from the start of transcription and which are involved in recognition and binding of RNA polymerase and other proteins to initiate transcription. A "plant promoter" is a promoter capable of initiating transcription in plant cells. A plant promoter can be, but does not have to be, a nucleic acid sequence originally isolated from a plant.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

A polynucleotide or polypeptide sequence is "heterologous to" an organism or a second sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). In another example, a CENH3 tail domain from a first species is heterologous to a CENH3 histone-fold domain from a second species.

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or *Current Protocols in Molecular Biology, Volumes* 1-3, John Wiley & Sons, Inc. (1994-1998)). In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

A "transgene" is used as the term is understood in the art and refers to a heterologous nucleic acid introduced into a cell by human molecular manipulation of the cell's genome (e.g., by molecular transformation). Thus a "transgenic plant" is a plant comprising a transgene, i.e., is a genetically-modified plant. The transgenic plant can be the initial plant into which the transgene was introduced as well as progeny thereof whose genome contain the transgene.

The term "corresponding" as used herein is used to mean "respective." For example, where it is said that a plant contains a recombinantly altered copy of a protein selected from A, B, and C, and the plant also contains a "corresponding" mutated endogenous copy of the gene selected from a gene encoding A, B, or C, if the plant contains a recombinantly altered protein A, the corresponding mutated endogenous copy would also be A. Alternatively, if the plant contains a recombinantly altered protein B, the corresponding mutated endogenous copy would also be B, etc.

The phrase "nucleic acid" or "polynucleotide sequence" refers to a single or double-stranded polymer of deoxyribonucleotide or ribonucleotide bases read from the 5' to the 3' end. Nucleic acids may also include modified nucleotides that permit correct read through by a polymerase, and/or formation of double-stranded duplexes, and do not significantly alter expression of a polypeptide encoded by that nucleic acid.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

The phrase "host cell" refers to a cell from any organism. Exemplary host cells are derived from plants, bacteria, yeast, fungi, insects or other animals. Methods for introducing polynucleotide sequences into various types of host cells are well known in the art.

An "expression cassette" refers to a nucleic acid construct, which when introduced into a host cell (e.g., a plant cell), results in transcription and/or translation of a RNA or polypeptide, respectively. An expression cassette can result in transcription without translation, for example, when an siRNA or other non-protein encoding RNA is transcribed.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Examples of algorithms that are suitable for determining percent sequence identity and sequence similarity are the BLAST and BLAST 2.0 algorithms, which are described in Altschul et al., *Nuc. Acids Res.* 25: 3389-3402 (1977), and Altschul et al., *J. Mol. Biol.* 215: 403-410 (1990), respectively. Software for performing BLAST analyses is publicly available on the Web through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89: 10915, (1989)) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90: 5873-5787, (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity to a designated reference sequence. Alternatively, percent identity can be any integer from 25% to 100%, for example, at least: 25%, 30%, 35%, 40%, 45%, 50%, 55%, 60%, 65%, 70%, 75%, 80%, 85%, 90%, 95%, or 99% compared to a reference sequence using the programs described herein; preferably BLAST using standard parameters, as described below. One of skill will recognize that the percent identity values above can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%. Percent identity of polypeptides can be any integer from 40% to 100%, for example, at least 40%, 45%, 50%, 55%, 60%, 65%, 70%, 75%, 80%, 85%, 90%, 95%, or 99%. In some embodiments, polypeptides that are "substantially similar" share sequences as noted above except that residue positions that are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, aspartic acid-glutamic acid, and asparagine-glutamine.

A "peptide sequence of sufficient length to block a polypeptide in an N-degron-dependent manner" refers to a peptide linked (typically by a peptide bond, optionally via an amino acid sequence linker) the amino terminus of a polypeptide comprising an N-degron such that the presence of the peptide sequence blocks degradation of the polypeptide by a cell that would otherwise degrade the polypeptide (e.g., via the N-end rule pathway). Removal of the peptide sequence (e.g., via cleavage) such that the N-degron is at or near the amino terminus of the polypeptide will allow for recognition of the N-degron sequence by the cell, thereby resulting in degradation of the polypeptide.

DETAILED DESCRIPTION

The inventors have determined that targeted use of N-degrons to degrade kinetochore proteins in a sex-specific manner in gametes of parent plants will result in plants that when selfed create some proportion (more than unmodified plants) of progeny with half the chromosome number of the parent plant. Thus, in situations in which the parent plant is a diploid plant, some progeny will be haploid.

A dormant (blocked) N-degron can be attached to the N-terminus of a protein of interest, i.e., a kinetochore protein. For example, the N-degron can be dormant due to linkage of a peptide sequence that interferes with the degron function, wherein the peptide and degron can be separated by a protease at a protease cleavage site between the peptide and degron. Thus, by controlling expression of a protease to certain cell types, one can control degron activity, and thus when and where the kinetochore protein is degraded. Upon expression of a site-specific protease, the dormant N-degron becomes deprotected (unblocked). The N-degron then targets itself and the attached protein (kinetochore protein) for proteasomal degradation through the N-end rule pathway.

Exemplary systems for degron regulation can be found in, e.g., Taxis et al., *Mol Syst Biol.* 5: 267 (2009). For example, in some embodiments, an N-degron/kinetochore fusion protein is provided comprising a blocking polypeptide sequence, a protease cleavage sequence, an N-degron amino acid sequence, and the kinetochore protein sequence. The blocking polypeptide will be of sufficient length to block the polypeptide in an N-degron-dependent manner, i.e., to block the N-degron sequence from being recognized by the degron-degradation pathway (e.g., N-end rule pathway) of the a cell. In some embodiments, the blocking polypeptide comprises more than 1, 2, 3, 4, 5, 6, 7, 8, 9, 10, amino acids, e.g., 5-500 amino acids. In some embodiments, the blocking polypeptide is a fluorescent polypeptide (for example, green fluorescent protein (GFP), Citrine, or tdTomato).

The protease cleavage sequence dividing the blocking polypeptide and the N-degron polypeptide will depend on the protease to be used. In embodiments in which tobacco etch virus (TEV) protease is used, the protease cleavage sequence can comprise, for example, ENLYFQ. It will be appreciated that other protease cleavage sequences can be used as well, so long as the protease targets or recognizes that particular sequences.

Any N-degron polypeptide sequence can be used so long as the N-degron polypeptide is targeted for destruction by the cell. Exemplary N-degron sequences include, for example, those described in Dougan et al. *Biochimica et Biophysica Acta (BBA)—Molecular Cell Research*, Volume 1823, Issue 1, January 2012, Pages 83-91; Duam et al., *Proc Natl Acad Sci USA.* 2014 Oct. 7; 111(40): 14619-14624; Taxis et al., *Mol Syst Biol.* 2009; 5: 267 (2009); Taxis, *Methods Mol Biol.* 2012; 832: 611-26; Daum, G. (2014). *Proc Natl Acad Sci USA*, 111(40), 14619-14624; Jungbluth, M., Renicke, C., & Taxis, C. (2010). *BMC Syst Biol*, 4, 176.

Exemplary kinetochore polypeptides can include, for example, CENH3, CENPC, MCM21, MIS12, NDC80, or NUF2.

CENH3 proteins are a well-characterized class of proteins that are variants of H3 histone proteins and that are specialized proteins associated with the centromere. CENH3 proteins are characterized by a variable tail domain, which does not form a rigid secondary structure, and a conserved histone fold domain made up of three α-helical regions connected by loop sections. Additional structural and functional features of CENH3 proteins can be found in, e.g., Cooper et al., *Mol Biol Evol.* 21(9): 1712-8 (2004); Malik et al., *Nat Struct Biol.* 10(11): 882-91 (2003); Black et al., *Curr Opin Cell Biol.* 20(1): 91-100 (2008). CENH3 proteins are one of the proteins that form the kinetochore complex.

A wide variety of CENH3 proteins have been identified. See, e.g., SEQ ID NOs:1-48 of U.S. Pat. No. 8,618,354. It will be appreciated that the above list is not intended to be exhaustive and that additional CENH3 sequences are available from genomic studies or can be identified from genomic databases or by well-known laboratory techniques. For example, where a particular plant or other organism species CENH3 is not readily available from a database, one can identify and clone the organism's CENH3 gene sequence using primers, which are optionally degenerate, based on conserved regions of other known CENH3 proteins.

As noted above, the CENH3 histone fold domain is conserved between CENH3 proteins from different species. The CENH3 histone fold domain can be distinguished by three α-helical regions connected by loop sections. While it will be appreciated that the exact location of the histone fold domain will vary in CENH3 proteins from other species, it will generally be found at the carboxyl terminus or proximate to a C-terminal tail, if any, of an endogenous (wildtype) CENH3 protein. Thus, in some embodiments, a CENH3 protein can be identified in an endogenous protein as having a carboxyl terminal domain substantially similar (e.g., at least 30%, 40%, 50%, 60%, 70%, 85%, 90%, 95% or more identity) to any of SEQ ID NO:s 49-94 of U.S. Pat. No. 8,618,354.

It is believed that other proteins that make up the kinetochore complex can also be targeted the same way as described herein for CENH3 and expressed in a plant that otherwise does not express the corresponding endogenous kinetochore complex protein to result in a viable plant that when selfed produces progeny having half the chromosomes (e.g., diploid to haploid) of the parent plant. In some embodiments, a diploid parent plant will generate haploid progeny at a certain frequency (e.g., at least 0.1, 0.5, 1, 5, 10, 20,%, or more). Exemplary non-CENH3 members of the kinetochore complex include, e.g., CENPC, MCM21, MIS12, NDC80, and NUF2.

The practice of the methods and compositions described herein will generally employ conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag.

Also provided are expression cassettes comprising a promoter operably linked to a polynucleotide encoding the N-degron/kinetochore fusion protein as described herein. By introduction of such expression cassettes into plants, transgenic plants can be generated that express the N-degron/kinetochore fusion protein. As described herein, the N-degron/kinetochore fusion protein should be expressed in male or female gametes or both. In some embodiments, the N-degron/kinetochore fusion protein is expressed from a constitutive promoter such that essentially all cells of the plant express the N-degron/kinetochore fusion protein. In such embodiments, the plant's endogenous corresponding kinetochore alleles can be knocked out or otherwise mutated such that the native kinetochore protein is inactive or not expressed at functional levels. In such cases, the only source of the particular kinetochore protein (e.g., CENH3, CENPC, MCM21, MIS12, NDC80, or NUF2) in the cell will be the N-degron/kinetochore fusion protein.

In some embodiments, the plant will also comprise a second expression cassette, the second expression cassette comprising a male-gamete- or female-gamete-specific promoter operable linked to a polynucleotide encoding a protease that targets the protease cleavage sequence of the N-degron/kinetochore fusion protein. As such the protease, when expressed, will cleave the N-degron/kinetochore fusion protein, thereby cleaving away the blocking polypeptide and allowing the N-degron to be available to tag the remaining portion of the N-degron/kinetochore fusion protein for destruction. An exemplary protease includes but is not limited to tobacco etch virus protease, for example as described in, e.g., Jungbluth, M., Renicke, C., & Taxis, C. (2010) *BMC Syst Biol*, 4, 176. Accordingly, the plant will have active kinetochores in all cells except male or except in female gametes. The resulting plant will generate progeny that have half the ploidy of the parent plant. Accordingly, inducible degron-mediated depletion of centromeric proteins can be used for chromosome elimination and haploid induction.

In some embodiments, the gamete-specific promoter is central cell, egg cell, or sperm cells-specific. Exemplary gametes specific promoters include, but are not limited to:
Arabidopsis EC1.1—egg cell-specific
Arabidopsis EC1.2—egg cell-specific
Arabidopsis FWA—central cell- and endosperm-specific
Arabidopsis DD25—central cell- and functional megaspore cell-specific
Arabidopsis DD45—egg cell-specific
Arabidopsis DD65—central cell- and endosperm-specific
Arabidopsis HTR10—sperm-cell specific
Arabidopsis DUO1—sperm-cell specific
Arabidopsis FM2—male and female gametophyte lineages
Arabidopsis ES1—female gametophyte lineage
Arabidopsis APG—male gametophyte lineage
Arabidopsis At5g01860—female gametophyte lineage.
In some embodiments, one or both expression cassettes comprises a DNA terminator sequence.
In some embodiments, the terminator is selected from, e.g., 35S terminator, pea rbcs-E9 terminator, Arabidopsis AtCenH3.

The methods and compositions described herein have at least two several advantages over current methods of haploid induction, including but not limited to:
1. By specific centromeric protein depletion in the gamete of one sex but not the other, genome elimination can be achieved through self-fertilization within the same bisexual flower rather than relying on cross fertilization between genetically different plants.

2. Depletion of centromeric proteins by protein degradation is a more rapid and efficient alternative to depletion by transcriptional or post-transcriptional repression.

Crossing plants that lack an endogenous kinetochore complex protein and have a degraded kinetochore protein due to N-degron-dependent degradation as described herein-either as a pollen or ovule parent to a plant that expresses an endogenous kinetochore complex protein (e.g., CENH3, CENPC, MCM21, MIS12, NDC80, or NUF2 protein) will result in at least some progeny (e.g., at least 0.1%, 0.5%, 1%, 5%, 10%, 20% or more) that are haploid and comprise only chromosomes from the plant that expresses the kinetochore complex protein. Thus, the present invention allows for the generation of haploid plants having all of its chromosomes from a plant of interest by crossing the plant of interest with a plant transgenically expressing the mutated kinetochore complex protein and collecting the resulting haploid seed.

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al., *Embo J.* 3: 2717-2722 (1984). Electroporation techniques are described in Fromm et al., *Proc. Natl. Acad. Sci. USA* 82: 5824 (1985). Biolistic transformation techniques are described in Klein et al., *Nature* 327: 70-73 (1987).

*Agrobacterium tumefaciens*-mediated transformation techniques, including disarming and use of binary vectors, are well described in the scientific literature. See, for example Horsch et al., *Science* 233: 496-498 (1984), and Fraley et al., *Proc. Natl. Acad. Sci. USA* 80: 4803 (1983).

Transformed plant cells which are derived by any of the above transformation techniques can be cultured to regenerate a whole plant which possesses the transformed genotype and thus the desired phenotype such as increased disease resistance compared to a control plant that was not transformed or transformed with an empty vector. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee et al., *Ann. Rev. of Plant Phys.* 38: 467-486 (1987).

The nucleic acids and encoded polypeptides of the invention can be used to confer the characteristics described herein, including the ability to generate haploid progeny, as described herein, on essentially any plant. Thus, the invention has use over a broad range of plants, including dicots or monocots, including e.g., species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panicum, Pennisetum, Persea, Pisum, Pyrus, Prunus, Raphanus, Secale, Senecio, Sinapis, Solanum, Sorghum, Trigonella, Triticum, Vitis, Vigna,* and, *Zea.*

As noted above, the plant expressing an endogenous wildtype CENH3 protein can be crossed as either the male or female parent.

Once generated, haploid plants can be used for a variety of useful endeavors, including but not limited to the generation of doubled haploid plants, which comprise an exact duplicate copy of chromosomes. Such doubled haploid plants are of particular use to speed plant breeding, for example. A wide variety of methods are known for generating doubled haploid organisms from haploid organisms.

Somatic haploid cells, haploid embryos, haploid seeds, or haploid plants produced from haploid seeds can be treated with a chromosome doubling agent. Homozygous double haploid plants can be regenerated from haploid cells by contacting the haploid cells, including but not limited to haploid callus, with chromosome doubling agents, such as colchicine, anti-microtubule herbicides, or nitrous oxide to create homozygous doubled haploid cells.

Methods of chromosome doubling are disclosed in, for example, U.S. Pat. Nos. 5,770,788; 7,135,615, and US Patent Publication No. 2004/0210959 and 2005/0289673; Antoine-Michard, S. et al., *Plant Cell, Tissue Organ Cult.,* Cordrecht, the Netherlands, Kluwer Academic Publishers 48(3): 203-207 (1997); Kato, A., Maize Genetics Cooperation Newsletter 1997, 36-37; and Wan, Y. et al., *Trends Genetics* 77: 889-892 (1989). Wan, Y. et al., *Trends Genetics* 81: 205-211 (1991), the disclosures of which are incorporated herein by reference. Methods can involve, for example, contacting the haploid cell with nitrous oxide, anti-microtubule herbicides, or colchicine. Optionally, the haploids can be transformed with a heterologous gene of interest, if desired.

Double haploid plants can be further crossed to other plants to generate F1, F2, or subsequent generations of plants with desired traits.

PROPHETIC EXAMPLE

CenH3 Constructs Incorporation the TEV Protease Recognition Site

A TEV site and N-degron can be appended to the N-terminus of CENH3. In some embodiments, the polypeptide sequence upstream (towards the amino terminus of the protein) of the TEV site will either contain:
a. A short peptide sequence that allows TEV protease binding and subsequent cleavage; or
b. A reporter protein Effectiveness of the N-degron in depleting CENH3 can be determined by testing ability to deplete GFP-CENH3 in co-transfected tobacco leaves and then by assaying ability to induce haploids in *Arabidopsis* plants with cell-specific expression of TEV protease.

Gamete-Specific CENH3 Depletion for Haploid Induction

Centromere strength conferred by CENH3 variants is displayed when gametes of different strengths fuse. Expression of TEV in only one of the gametes should result in haploid induction during selfing. As CENH3 is naturally depleted in the egg and central cell during gametophyte development, it may be necessary to activate TEV earlier in the female lineage in order for N-degron-mediated depletion to have an effect.

In some embodiments, N-degron-mediated depletion is performed on the male side. Even if haploid induction does not occur efficiently with a CENH3-variant based male haploid inducer, sperm cell-specific CENH3-depletion strategies may lead to substantial haploid induction.

Note: Yeast- and Arabidopsis-optimized versions of TEV protease and the degron construct differ, though the degron and TEV site DNA sequences themselves are identical. In addition to SNPs in the protease domain, the Arabidopsis-optimized TEV protease lacks the P14 and myc sequences (see, Taxis, C., Stier, G., Spadaccini, R., & Knop, M. (2009). Efficient protein depletion by genetically controlled deprotection of a dormant N-degron. Mol Syst Biol, 5, 267) in the yeast-optimized sequence and instead contains a tdTomato fluorophore at the N terminus of the TEV protease. As the Arabidopsis-optimized protease lacks the P14 domain, the SF3b sequence was not included in the Arabidopsis-optimized degron construct. Also, different peptide spacers are used.

A. TEV Protease and Degron Sequences (Yeast-Optimized)

```
>TEV_protease_DNA_sequence_for_yeast:P14-myc-TEV234-stop (SEQ ID
NO: 1)
ATGGCGATGCAAGCGGCCAAGAGGGCGAACATTCGTCTTCCACCTGAAGTAAATAGAATATTGT
ATATAAGAAATTTGCCATACAAATCACAGCTGAAGAAATGTATGATATATTTGGGAAATATGG
ACCTATTCGTCAAATCAGAGTGGGGAACACACCTGAAACTAGAGGAACAGCTTATGTGGTCTAT
GAGGACATCTTTGATGCCAAGAATGCATGTGATCACCTATCGGGATTCAATGTTTGTAACAGAT
ACCTTGTGGTTTTGTACTATAATGCCAACAGGGCATTTCAGAAGATGGACACAAAGAAGAAGGA
GGAACAGTTGAAGCTTTTGAAGGAGAAATATGGCATCAACACATATCCTCCCAAGATGGAACAA
AAGTTGATATCTGAAGAAGACTTGCCCATGAGCGGCCTGGTGCCGAGAGGCAGCGCCATGGGAG
AAAGCTTGTTTAAGGGACCACGTGATTACAACCCGATATCGAGCGACATTTGTCATTTGACGAA
TGAATCTGATGGGCACACAACATCGTTGTATGGTATTGGATTTGGTCCCTTCATCATTACAAAC
AAGCACTTGTTTCGTAGAAATAATGGAACACTGTTGGTCCAATCACTACATGGTGTATTCAAGG
TCAAGGACACCACGACTTTGCAACAACACTTGGTTGATGGGAGGGACATGATGATTATTAGAAT
GCCTAAGGATTTCCCACCATTTCCTCAAAAGCTGAAATTTAGAGAGCCACAAAGGGAAGAGAGA
ATATGTCTTGTGACAACCAACTTCCAAGCTAAGAGCATGTCTAGCATGGTGTCAGACACTAGTT
GCACATTCCCTTCATCTGATGGTATATTCTGGAAGCATTGGATTCAAACCAAGGATGGGCAGTG
TGGCAGTCCATTAGTATCAACTAGAGATGGGTTCATTGTTGGTATACACTCAGCATCGAATTTC
```

```
ACCAACACAAACAATTATTTCACAAGCGTGCCGAAAAACTTCATGGAATTGTTGACAAATCAGG
AGGCGCAGCAGTGGGTTAGTGGTTGGAGATTAAACGCTGACTCAGTATTGTGGGGGGCCATAA
AGTTTTCATGGTTAAACCTGAAGAACCTTTTCAGCCAGTTAAGGAAGCGACTCAATTGTAA

P14-(SEQ ID NO: 2)
ATGGCGATGCAAGCGGCCAAGAGGGCGAACATTCGTCTTCCACCTGAAGTAAATAGAATATTGT
ATATAAGAAATTTGCCATACAAAATCACAGCTGAAGAAATGTATGATATATTTGGGAAATATGG
ACCTATTCGTCAAATCAGAGTGGGGAACACACCTGAAACTAGAGGAACAGCTTATGTGGTCTAT
GAGGACATCTTTGATGCCAAGAATGCATGTGATCACCTATCGGGATTCAATGTTTGTAACAGAT
ACCTTGTGGTTTTGTACTATAATGCCAACAGGGCATTTCAGAAGATGGACACAAAGAAGAAGGA
GGAACAGTTGAAGCTTTTGAAGGAGAAATATGGCATCAACACATATCCTCCCAAG myc-(SEQ ID NO: 3)
ATGGAACAAAAGTTGATATCTGAAGAAGACTTGCCCATGAGCGGCCTGGTGCCGAGAGGCAGCG
CC TEV234-(SEQ ID NO: 4)
ATGGGAGAAAGCTTGTTTAAGGGACCACGTGATTACAACCCGATATCGAGCGACATTTGTCATT
TGACGAATGAATCTGATGGGCACACAACATCGTTGTATGGTATTGGATTTGGTCCCTTCATCAT
TACAAACAAGCACTTGTTTCGTAGAAATAATGGAACACTGTTGGTCCAATCACTACATGGTGTA
TTCAAGGTCAAGGACACCACGACTTTGCAACAACACTTGGTTGATGGGAGGGACATGATGATTA
TTAGAATGCCTAAGGATTTCCCACCATTTCCTCAAAAGCTGAAATTTAGAGAGCCACAAAGGGA
AGAGAGAATATGTCTTGTGACAACCAACTTCCAAGCTAAGAGCATGTCTAGCATGGTGTCAGAC
ACTAGTTGCACATTCCCTTCATCTGATGGTATATTCTGGAAGCATTGGATTCAAACCAAGGATG
GGCAGTGTGGCAGTCCATTAGTATCAACTAGAGATGGGTTCATTGTTGGTATACACTCAGCATC
GAATTTCACCAACACAAACAATTATTTCACAAGCGTGCCGAAAAACTTCATGGAATTGTTGACA
AATCAGGAGGCGCAGCAGTGGGTTAGTGGTTGGAGATTAAACGCTGACTCAGTATTGTGGGGGG
GCCATAAAGTTTTCATGGTTAAACCTGAAGAACCTTTTCAGCCAGTTAAGGAAGCGACTCAATT
G
Stop-TAA >TEV_protease_protein_sequence_for_yeast:P14-myc-TEV234-stop
(SEQ ID NO: 5)
MAMQAAKRANIRLPPEVNRILYIRNLPYKITAEEMYDIFGKYGPIRQIRVGNTPETRGTAYVVY
EDIFDAKNACDHLSGFNVCNRYLVVLYYNANRAFQKMDTKKKEEQLKLLKEKYGINTYPPKMEQ
KLISEEDLPMSGLVPRGSAMGESLFKGPRDYNPISSDICHLTNESDGHTTSLYGIGFGPFIITN
KHLFRRNNGTLLVQSLHGVFKVKDTTTLQQHLVDGRDMMIIRMPKDFPPFPQKLKFREPQREER
ICLVTINFQAKSMSSMVSDTSCTFPSSDGIFWKHWIQTKDGQCGSPLVSTRDGFIVGIHSASNF
TNTNNYFTSVPKNFMELLTNQEAQQWVSGWRLNADSVLWGGHKVFMVKPEEPFQPVKEATQLStop

P14-(SEQ ID NO: 6)
MAMQAAKRANIRLPPEVNRILYIRNLPYKITAEEMYDIFGKYGPIRQIRVGNTPETRGTAYVVY
EDIFDAKNACDHLSGFNVCNRYLVVLYYNANRAFQKMDTKKKEEQLKLLKEKYGINTYPPK myc-MEQKLISEEDLPMSGLVPRGSA (SEQ ID NO: 7)

TEV234-(SEQ ID NO: 8)
MGESLFKGPRDYNPISSDICHLTNESDGHTTSLYGIGFGPFIITNKHLFRRNNGTLLVQSLHGV
FKVKDITTLQQHLVDGRDMMIIRMPKDFPPFPQKLKFREPQREERICLVTINFQAKSMSSMVSD
TSCTFPSSDGIFWKHWIQTKDGQCGSPLVSTRDGFIVGIHSASNFTNTNNYFTSVPKNFMELLT
NQEAQQWVSGWRLNADSVLWGGHKVFMVKPEEPFQPVKEATQL
Stop

>Degron_construct_DNA_sequence_for_yeast:GFP-cODC1-spacer-
TEVrec-Ndegron-spacer-SF3b-spacer-mKATE-stop (SEQ ID NO: 9)
ATGTCTAAAGGTGAAGAATTATTCACTGGTGTTGTCCCAATTTTGGTTGAATTAGATGGTGATG
TTAATGGTCACAAATTTTCTGTCTCCGGTGAAGGTGAAGGTGATGCTACTTACGGTAAATTGAC
CTTAAAATTTATTTGTACTACTGGTAAATTGCCAGTTCCATGGCCAACCTTAGTCACTACTTTC
GGTTATGGTGTTCAATGTTTTGCGAGATACCCAGATCATATGAAACAACATGACTTTTTCAAGT
CTGCCATGCCAGAAGGTTATGTTCAAGAAAGAACTATTTTTTTCAAAGATGACGGTAACTACAA
GACCAGAGCTGAAGTCAAGTTTGAAGGTGATACCTTAGTTAATAGAATCGAATTAAAAGGTATT
GATTTTAAAGAAGATGGTAACATTTTAGGTCACAAATTGGAATACAACTATAACTCTCACAATG
TTTACATCATGGCTGACAAACAAAAGAATGGTATCAAAGTTAACTTCAAAATTAGACACAACAT
TGAAGATGGTTCTGTTCAATTAGCTGACCATTATCAACAAAATACTCCAATTGGTGATGGTCCA
GTCTTGTTACCAGACAACCATTACTTATCCACTCAATCTGCCTTATCCAAAGATCCAAACGAAA
AGAGAGACCACATGGTCTTGTTAGAATTTGTTACTGCTGCTGGTATTACCCATGGTATGGATGA
ATTGTACAAATTGCCAATGTCTTGTGCACAAGAATCTATTACTTCTTTGTACAAGAAGGCTGGT
TCTGAAAACTTGTACTTCCAATTCCACAAGTCTGGTGCTTGGAAGTTGCCAGTTTCTTTGGTTA
AGAGAGGGATCGATAAGCTTGATTATAAAGAACAGCTTCAGGCTTGGCGGTGGGAAAGAGAAAT
TGATGAGAGAAATCGCCCACTTTCTGATGAGGAATTAGATGCTATGTTCCCAGAAGGCTATAAG
GTACTTCCTCCTCCAGCTGGTTATGTTCCTATTCGAACTCCAGCTCATATGGATCGAATTCCTG
CAGTAGCAGGTGCTGGTGCTGGTGCTGGAGCAATGTCTGAATTAATTAAAGAAAATATGCATAT
GAAATTATATATGGAAGGTACAGTTAATAATCATCATTTTAAATGTACATCTGAAGGTGAAGGT
AAACCATATGAAGGTACACAAACAATGAGAATTAAAGTTGTTGAAGGTGGTCCATTACCATTTG
CTTTTGATATTTTAGCTACATCTTTTATGTATGGTTCTAAGACATTTATTAATCATACACAAGG
TATTCCAGATTTTTTTAAACAATCTTTTCCAGAAGGTTTTACATGGGAAAGAGTTACAACATAT
GAAGATGGTGGTGTTTTAACAGCTACACAAGATACATCTTTACAAGATGGTTGTTTAATTTATA
ATGTTAAAATTAGAGGTGTTAATTTTCCATCTAATGGTCCAGTTATGCAAAAAAAAACATTAGG
TTGGGAAGCTTCTACAGAAATGTTATATCCAGCTGATGGTGGTTTAGAAGGTAGGTCTGATATG
```

```
GCTTTAAAATTAGTTGGTGGTGGTCATTTAATTTGTAATTTGAAAACAACATATAGGTCTAAAA
AACCAGCTAAAAATTTAAAAATGCCAGGTGTTTATTATGTTGATAGAAGATTAGAAAGAATTAA
AGAAGCTGATAAAGAAACATATGTTGAACAACATGAAGTTGCTGTTGCTAGATATTGTGATTTA
CCATCTAAATTAGGTCATAAAGGATCCTAA
```

GFP-(SEQ ID NO: 10)
```
ATGTCTAAAGGTGAAGAATTATTCACTGGTGTTGTCCCAATTTTGGTTGAATTAGATGGTGATG
TTAATGGTCACAAATTTTCTGTCTCCGGTGAAGGTGAAGGTGATGCTACTTACGGTAAATTGAC
CTTAAAATTTATTTGTACTACTGGTAAATTGCCAGTTCCATGGCCAACCTTAGTCACTACTTTC
GGTTATGGTGTTCAATGTTTTGCGAGATACCCAGATCATATGAAACAACATGACTTTTTCAAGT
CTGCCATGCCAGAAGGTTATGTTCAAGAAAGAACTATTTTTTTCAAAGATGACGGTAACTACAA
GACCAGAGCTGAAGTCAAGTTTGAAGGTGATACCTTAGTTAATAGAATCGAATTAAAAGGTATT
GATTTTAAAGAAGATGGTAACATTTTAGGTCACAAATTGGAATACAACTATAACTCTCACAATG
TTTACATCATGGCTGACAAACAAAAGAATGGTATCAAAGTTAACTTCAAAATTAGACACAACAT
TGAAGATGGTTCTGTTCAATTAGCTGACCATTATCAACAAAATACTCCAATTGGTGATGGTCCA
GTCTTGTTACCAGACAACCATTACTTATCCACTCAATCTGCCTTATCCAAAGATCCAAACGAAA
AGAGAGACCACATGGTCTTGTTAGAATTTGTTACTGCTGCTGGTATTACCCATGGTATGGATGA
ATTGTACAAA
``` cODC1-TTGCCAATGTCTTGTGCACAAGAA (SEQ ID NO: 11)

spacer-TCTATTACTTCTTTGTACAAGAAGGCTGGTTCT (SEQ ID NO: 12)

TEVrec-GAAAACTTGTACTTCCAATTC (SEQ ID NO: 13)

Ndegron-CACAAGTCTGGTGCTTGGAAGTTGCCAGTTTCTTTGGTTAAG (SEQ ID NO: 14)

spacer-AGAGGGATCGATAAGCTTGATTATAAA (SEQ ID NO: 15)

SF3b-(SEQ ID NO: 16)
```
GAACAGCTTCAGGCTTGGCGGTGGGAAAGAGAAATTGATGAGAGAAATCGCCCACTTTCTGATG
AGGAATTAGATGCTATGTTCCCAGAAGGATATAAGGTACTTCCTCCTCCAGCTGGTTATGTTCC
TATTCGAACTCCAGCT
``` spacer-CATATGGATCGAATTCCTGCAGTA (SEQ ID NO: 17)

TEV234-(SEQ ID NO: 18)
```
GCAGGTGCTGGTGCTGGTGCTGGAGCAATGTCTGAATTAATTAAAGAAAATATGCATATGAAAT
TATATATGGAAGGTACAGTTAATAATCATCATTTTAAATGTACATCTGAAGGTGAAGGTAAACC
ATATGAAGGTACACAAACAATGAGAATTAAAGTTGTTGAAGGTGGTCCATTACCATTTGCTTTT
GATATTTTAGCTACATCTTTTATGTATGGTTCTAAGACATTTATTAATCATACAACAAGGTATTC
CAGATTTTTTTAAACAATCTTTTCCAGAAGGTTTTACATGGGAAGAGTTACAACATATGAAGA
TGGTGGTGTTTTAACAGCTACACAAGATACATCTTTACAAGATGGTTGTTTAATTTATAATGTT
AAAATTAGAGGTGTTAATTTTCCATCTAATGGTCCAGTTATGCAAAAAAAAACATTAGGTTGGG
AAGCTTCTACAGAAATGTTATATCCAGCTGATGGTGGTTTAGAAGGTAGGTCTGATATGGCTTT
AAAATTAGTTGGTGGTGGTCATTTAATTTGTAATTTGAAAACAACATATAGGTCTAAAAAACCA
GCTAAAAATTTAAAAATGCCAGGTGTTTATTATGTTGATAGAGAATTAGAAAGAATTAAAGAAG
CTGATAAAGAAACATATGTTGAACAACATGAAGTTGCTGTTGCTAGATATTGTGATTTACCATC
TAAATTAGGTCATAAAGGATCC
```
stop-TAA >Degron_protein_DNA_sequence_for_yeast:GFP-cODC1-spacer-TEVrec-
Ndegron-spacer-SF3b-spacer-mKATE-stop
GFP-(SEQ ID NO: 19)
MSKGEELFTGVVPILVELDGDVNGHKFSVSGEGEGDATYGKLTLKFICTTGKLPVPWPTLVTTF
GYGVQCFARYPDHMKQHDFFKSAMPEGYVQERTIFFKDDGNYKTRAEVKFEGDTLVNRIELKGI
DFKEDGNILGHKLEYNYNSHNVYIMADKQKNGIKVNFKIRHNIEDGSVQLADHYQQNTPIGDGP
VLLPDNHYLSTQSALSKDPNEKRDHMVLLEFVTAAGITHGMDELYKLPMSCAQESITSLYKKAG
SENLYFQFHKSGAWKLPVSLVKRGIDKLDYKEQLQAWRWEREIDERNRPLSDEELDAMFPEGYK
VLPPPAGYVPIRTPAHMDRIPAVAGAGAGAGAMSELIKENMHMKLYMEGTVNNHHFKCTSEGEG
KPYEGTQTMRIKVVEGGPLPFAFDILATSF MYGSKTFINHTQGIPDFFKQSFPEGFTWERVTTY
EDGGVLTATQDTSLQDGCLIYNVKIRGVNFPSNGPVMQKKTLGWEASTEMLYPADGGLEGRSDM
ALKLVGGGHLICNLKTTYRSKKPAKNLKMPGVYYVDRRLERIKEADKETYVEQHEVAVARYCDL
PSKLGHKGSStop

GFP-(SEQ ID NO: 20)
MSKGEELFTGVVPILVELDGDVNGHKFSVSGEGEGDATYGKLTLKFICTTGKLPVPWPTLVTTF
GYGVQCFARYPDHMKQHDFFKSAMPEGYVQERTIFFKDDGNYKTRAEVKFEGDTLVNRIELKGI
DFKEDGNILGHKLEYNYNSHNVYIMADKQKNGIKVNFKIRHNIEDGSVQLADHYQQNTPIGDGP
VLLPDNHYLSTQSALSKDPNEKRDHMVLLEFVTAAGITHGMDELYK cODC1-LPMSCAQE (SEQ ID NO: 21)

spacer-SITSLYKKAGS (SEQ ID NO: 22)

TEVrec-ENLYFQF (SEQ ID NO: 23)

Ndegron-HKSGAWKLPVSLVK (SEQ ID NO: 24)

-continued

```
spacer-RGIDKLDYK (SEQ ID NO: 25)

SF3b-EQLQAWRWEREIDERNRPLSDEELDAMFPEGYKVLPPPAGYVPIRTPA (SEQ ID
NO: 26)

spacer-HMDRIPAV (SEQ ID NO: 27)

mKATE-(SEQ ID NO: 28)
AGAGAGAGAMSELIKENMHMKLYMEGTVNNHHFKCTSEGEGKPYEGTQTMRIKVVEGGPLPFAF
DILATSFMYGSKTFINHTQGIPDFFKQSFPEGFTWERVTTYEDGGVLTATQDTSLQDGCLIYNV
KIRGVNFPSNGPVMQKKTLGWEASTEMLYPADGGLEGRSDMALKLVGGGHLICNLKTTYRSKKP
AKNLKMPGVYYVDRRLERIKEADKETYVEQHEVAVARYCDLPSKLGHKGS
Stop
```

B. TEV Protease and Degron Sequences
(Arabidopsis-Optimized)

```
>TEV_protease_DNA_sequence_for_Arabidopsis:tdTomato-spacer-TEV-
stop
tdTomato-(SEQ ID NO: 29)
ATGGTGAGCAAGGGCGAGGAGGTCATCAAAGAGTTCATGCGCTTCAAGGTGCGCATGGAGGGCT
CCATGAACGGCCACGAGTTCGAGATCGAGGGCGAGGGCGAGGGCCGCCCCTACGAGGGCACCCA
GACCGCCAAGCTGAAGGTGACCAAGGGCGGCCCCCTGCCCTTCGCCTGGGACATCCTGTCCCCC
CAGTTCATGTACGGCTCCAAGGCGTACGTGAAGCACCCCGCCGACATCCCCGATTACAAGAAGC
TGTCCTTCCCCGAGGGCTTCAAGTGGGAGCGCGTGATGAACTTCGAGGACGGCGGTCTGGTGAC
CGTGACCCAGGACTCCTCCCTGCAGGACGGCACGCTGATCTACAAGGTGAAGATGCGCGGCACC
AACTTCCCCCCCGACGGCCCCGTAATGCAGAAGAAGACCATGGGCTGGGAGGCCTCCACCGAGC
GCCTGTACCCCGCGACGGCGTGCTGAAGGGCGAGATCCACCAGGCCCTGAAGCTGAAGGACGG
CGGCCACTACCTGGTGGAGTTCAAGACCATCTACATGGCCAAGAAGCCCGTGCAACTGCCCGGC
TACTACTACGTGGACACCAAGCTGGACATCACCTCCCACAACGAGGACTACACCATCGTGGAAC
AGTACGAGCGCTCCGAGGGCCGCCACCACCTGTTCCTGGGGCATGGCACCGGCAGCACCGGCAG
CGGCAGCTCCGGCACCGCCTCCTCCGAGGACAACAACATGGCCGTCATCAAAGAGTTCATGCGC
TTCAAGGTGCGCATGGAGGGCTCCATGAACGGCCACGAGTTCGAGATCGAGGGCGAGGGCGAGG
GCCGCCCCTACGAGGGCACCCAGACCGCCAAGCTGAAGGTGACCAAGGGCGGCCCCCTGCCCTT
CGCCTGGGACATCCTGTCCCCCCAGTTCATGTACGGCTCCAAGGCGTACGTGAAGCACCCCGCC
GACATCCCCGATTACAAGAAGCTGTCCTTCCCCGAGGGCTTCAAGTGGGAGCGCGTGATGAACT
TCGAGGACGGCGGTCTGGTGACCGTGACCCAGGACTCCTCCCTGCAGGACGGCACGCTGATCTA
CAAGGTGAAGATGCGCGGCACCAACTTCCCCCCCGACGGCCCCGTAATGCAGAAGAAGACCATG
GGCTGGGAGGCCTCCACCGAGCGCCTGTACCCCGCGACGGCGTGCTGAAGGGCGAGATCCAC
AGGCCCTGAAGCTGAAGGACGGCGGCCACTACCTGGTGGAGTTCAAGACCATCTACATGGCCAA
GAAGCCCGTGCAACTGCCCGGCTACTACTACGTGGACACCAAGCTGGACATCACCTCCCACAAC
GAGGACTACACCATCGTGGAACAGTACGAGCGCTCCGAGGGCCGCCACCACCTGTTCCTGTACG
GCATGGACGAGCTGTACAAG spacer-(SEQ ID NO: 30)
GCCGCTAGTGCGATCGCATCAGGGAGTGGTTCCGGAAGCGGCTCTGGATCGGGCTCAGGGAGTG
GTTCCGGCAGCGGCTCTGGATCGGCGGCCGCTGCA TEV-(SEQ ID NO: 31)
ATGGGAGAAAGCTTGTTTAAGGGGCCGCGTGATTACAACCCGATATCGAGCACCATTTGTCATT
TGACGAATGAATCTGATGGGCACACAACATCGTTGTATGGTATTGGATTTGGTCCCTTCATCAT
TACAAACAAGCACTTGTTTAGAAGAAATAATGGAACACTGGTGGTCAATCATCTACATGGTGTA
TTCAAGGTCAAGAACACCACGACTTTGCAACAACACCTCATTGATGGGAGGGACATGATAATTA
TTCGCATGCCTAAGGATTTCCCACCCATTTCCTCAAAAGCTGAAATTTAGAGAGCCACAAGGGA
AGAGCGCATATGTCTTGTGACAACCAACTTCCAAACTAAGAGCATGTCTAGCATGGTGTCAGAC
ACTAGTTGCACATTCCCTTCAGGAGATGGCATATTCTGGAAGCATTGGATTCAAACCAAGGATG
GGCAGTGTGGCAGTCCATTAGTATCAACTAGAGATGGGTTCATTGTTGGTATACACTCAGCATC
GAATTTCACCAACACAAACAATTATTTCACAAGCGTGCCGAAAAACTTCATGGAATTGTTGACA
AATCAGGAGGCGCAGCAGTGGGTTAGTGGTTGGCGATTAAATGCTGACTCAGTATTGTGGGGGG
GCCATAAAGTTTTCATGGTGAAACCTGAAGAGCCTTTCAGCCAGTTAAGGAAGCGACTCAACT
CATGAAT
STOP-TGA >TEV_protease_protein_sequence_for_Arabidopsis:tdTomato-spacer-
TEV
tdTomato-(SEQ ID NO: 32)
MVSKGEEVIKEFMRFKVRMEGSMNGHEFEIEGEGEGRPYEGTQTAKLKVTKGGPLPFAWDILSP
QFMYGSKAYVKHPADIPDYKKLSFPEGFKWERVMNFEDGGLVTVTQDSSLQDGTLIYKVKMRGT
NFPPDGPVMQKKTMGWEASTERLYPRDGVLKGEIHQALKLKDGGHYLVEFKTIYMAKKPVQLPG
YYYVDTKLDITSHNEDYTIVEQYERSEGRHHLFLGHGTGSTGSGSSGTASSEDNNMAVIKEFMR
FKVRMEGSMNGHEFEIEGEGEGRPYEGTQTAKLKVTKGGPLPFAWDILSPQFMYGSKAYVKHPA
DIPDYKKLSFPEGFKWERVMNFEDGGLVTVTQDSSLQDGTLIYKVKMRGINFPPDGPVMQKKTM
GWEASTERLYPRDGVLKGEIHQALKLKDGGHYLVEFKTIYMAKKPVQLPGYYYVDTKLDITSHN
EDYTIVEQYERSEGRHHLFLYGMDELYK
``` spacer-(SEQ ID NO: 33)
AASAIASGSGSGSGSGSGSGSGSGSGSAAAA

TEV-(SEQ ID NO: 34)
MGESLFKGPRDYNPISSTICHLTNESDGHTTSLYGIGFGPFIITNKHLFRRNNGTLVVQSLHGV
FKVKNTTTLQQHLIDGRDMIIIRMPKDFPPFPQKLKFREPQREERICLVTTNFQTKSMSSMVSD
TSCTFPSGDGIFWKHWIQTKDGQCGSPLVSTRDGFIVGIHSASNFTNTNNYFTSVPKNFMELLT
NQEAQQWVSGWRLNADSVLWGGHKVFMVKPEEPFQPVKEATQLMN*

>Degron_DNA_sequence_for_Arabidopsis:Citrine-spacer-TEVsite-
Ndeg-spacer-WUS (SEQ ID NO: 35)
ATGGTGAGCAAGGGCGAGGAGCTGTTCACCGGGGTGGTGCCCATCCTGGTCGAGCTGGACGGCG
ACGTAAACGGCCACAAGTTCAGCGTGTCCGGCGAGGGCGAGGGCGATGCCACCTACGGCAAGCT
GACCCTGAAGTTCATCTGCACCACCGGCAAGCTGCCCGTGCCCTGGCCCACCCTCGTGACCACC
TTCGGCTACGGCCTGATGTGCTTCGCCCGCTACCCCGACCACATGAAGCAGCACGACTTCTTCA
AGTCCGCCATGCCCGAAGGCTACGTCCAGGAGCGCACCATCTTCTTCAAGGACGACGGCAACTA
CAAGACCCGCGCCGAGGTGAAGTTCGAGGGCGACACCCTGGTGAACCGCATCGAGCTGAAGGGC
ATCGACTTCAAGGAGGACGGCAACATCCTGGGGCACAAGCTGGAGTACAACTACAACAGCCACA
ACGTCTATATCATGGCCGACAAGCAGAAGAACGGCATCAAGGTGAACTTCAAGATCCGCCACAA
CATCGAGGACGGCAGCGTGCAGCTCGCCGACCACTACCAGCAGAACACCCCCATCGGCGACGGC
CCCGTGCTGCTGCCCGACAACCACTACCTGAGCTACCAGTCCGCCCTGAGCAAAGACCCCAACG
AGAAGCGCGATCACATGGTCCTGCTGGAGTTCGTGACCGCCGCCGGGATCACTCTCGGCATGGA
CGAGCTGTACAAGGCAGCGGCCGCTTCAGGGAGTGGTTCCGGAAGCGAAAACTTGTACTTCCAA
TTCCACAAGTCTGGTGCTTGGAAGTTGCCAGTTTCTTTGGTTAAGGGGAGTGGTTCCGGCAGCG
GCTCTGGATCGTCAATTGCTATGGAGCCGCCACAGCATCAGCATCATCATCATCAAGCCGACCA
AGAAAGCGGCAACAACAACAACAACAAGTCCGGCTCTGGTGGTTACACGTGTCGCCAGACCAGC
ACGAGGTGGACACCGACGACGGAGCAAATCAAAATCCTCAAAGAACTTTACTACAACAATGCAA
TCCGGTCACCAACAGCCGATCAGATCCAGAAGATCACTGCAAGGCTGAGACAGTTCGGAAAGAT
TGAGGGCAAGAACGTCTTTTACTGGTTCCAGAACCATAAGGCTCGTGAGCGTCAGAAGAAGAGA
TTCAACGGAACAAACATGACCACACCATCTTCATCACCCAACTCGGTTATGATGGCGGCTAACG
ATCATTATCATCCTCTACTTCACCATCATCACGGTGTTCCCATGCAGAGACCTGCTAATTCCGT
CAACGTTAAACTTAACCAAGACCATCATCTCTATCATCATAACAAGCCATATCCCAGCTTCAAT
AACGGGAATTTAAATCATGCAAGCTCAGGTACTGAATGTGGTGTTGTTAATGCTTCTAATGGCT
ACATGAGTAGCCATGTCTATGGATCTATGGAACAAGACTGTTCTATGAATTACAACAACGTAGG
TGGAGGATGGGCAAACATGGATCATCATTACTCATCTGCACCTTACAACTTCTTCGATAGAGCA
AAGCCTCTGTTTGGTCTAGAAGGTCATCAAGAAGAAGAAGAATGTGGTGGCGATGCTTATCTGG
AACATCGACGTACGCTTCCTCTCTTCCCTATGCACGGTGAAGATCACATCAACGGTGGTAGTGG
CGCCATCTGGAAGTATGGCCAATCGGAAGTTCGCCCTTGCGCTTCTCTTGAGCTACGTCTGAAC Citrine-(SEQ ID NO: 36)
ATGGTGAGCAAGGGCGAGGAGCTGTTCACCGGGGTGGTGCCCATCCTGGTCGAGCTGGACGGCG
ACGTAAACGGCCACAAGTTCAGCGTGTCCGGCGAGGGCGAGGGCGATGCCACCTACGGCAAGCT
GACCCTGAAGTTCATCTGCACCACCGGCAAGCTGCCCGTGCCCTGGCCCACCCTCGTGACCACC
TTCGGCTACGGCCTGATGTGCTTCGCCCGCTACCCCGACCACATGAAGCAGCACGACTTCTTCA
AGTCCGCCATGCCCGAAGGCTACGTCCAGGAGCGCACCATCTTCTTCAAGGACGACGGCAACTA
CAAGACCCGCGCCGAGGTGAAGTTCGAGGGCGACACCCTGGTGAACCGCATCGAGCTGAAGGGC
ATCGACTTCAAGGAGGACGGCAACATCCTGGGGCACAAGCTGGAGTACAACTACAACAGCCACA
ACGTCTATATCATGGCCGACAAGCAGAAGAACGGCATCAAGGTGAACTTCAAGATCCGCCACAA
CATCGAGGACGGCAGCGTGCAGCTCGCCGACCACTACCAGCAGAACACCCCCATCGGCGACGGC
CCCGTGCTGCTGCCCGACAACCACTACCTGAGCTACCAGTCCGCCCTGAGCAAAGACCCCAACG
AGAAGCGCGATCACATGGTCCTGCTGGAGTTCGTGACCGCCGCCGGGATCACTCTCGGCATGGA
CGAGCTGTACAAG spacer-GCAGCGGCCGCTTCAGGGAGTGGTTCCGGAAGC (SEQ ID NO: 37)

TEVsite-GAAAACTTGTACTTCCAATTC (SEQ ID NO: 38)

Ndeg-CACAAGTCTGGTGCTTGGAAGTTGCCAGTTTCTTTGGTTAAG (SEQ ID NO: 39)

spacer-GGGAGTGGTTCCGGCAGCGGCTCTGGATCGTCAATTGCT (SEQ ID NO: 40)

WUS (SEQ ID NO: 41)-
ATGGAGCCGCCACAGCATCAGCATCATCATCATCAAGCCGACCAAGAAAGCGGCAACAACAACA
ACAACAAGTCCGGCTCTGGTGGTTACACGTGTCGCCAGACCAGCACGAGGTGGACACCGACGAC
GGAGCAAATCAAAATCCTCAAAGAACTTTACTACAACAATGCAATCCGGTCACCAACAGCCGAT
CAGATCCAGAAGATCACTGCAAGGCTGAGACAGTTCGGAAAGATTGAGGGCAAGAACGTCTTTT
ACTGGTTCCAGAACCATAAGGCTCGTGAGCGTCAGAAGAAGAGATTCAACGGAACAAACATGAC
CACACCATCTTCATCACCCAACTCGGTTATGATGGCGGCTAACGATCATTATCATCCTCTACTT
CACCATCATCACGGTGTTCCCATGCAGAGACCTGCTAATTCCGTCAACGTTAAACTTAACCAAG
ACCATCATCTCTATCATCATAACAAGCCATATCCCAGCTTCAATAACGGGAATTTAAATCATGC
AAGCTCAGGTACTGAATGTGGTGTTGTTAATGCTTCTAATGGCTACATGAGTAGCCATGTCTAT
GGATCTATGGAACAAGACTGTTCTATGAATTACAACAACGTAGGTGGAGGATGGGCAAACATGG
ATCATCATTACTCATCTGCACCTTACAACTTCTTCGATAGAGCAAAGCCTCTGTTTGGTCTAGA
AGGTCATCAAGAAGAAGAAGAATGTGGTGGCGATGCTTATCTGGAACATCGACGTACGCTTCCT
CTCTTCCCTATGCACGGTGAAGATCACATCAACGGTGGTAGTGGCGCCATCTGGAAGTATGGCC
AATCGGAAGTTCGCCCTTGCGCTTCTCTTGAGCTACGTCTGAAC

-continued

>Degron_protein_sequence_for_Arabidopsis:Citrine-spacer-TEVsite-
Ndeg-spacer-WUS (SEQ ID NO: 42)
MVSKGEELFTGVVPILVELDGDVNGHKFSVSGEGEGDATYGKLTLKFICTTGKLPVPWPTLVTT
FGYGLMCFARYPDHMKQHDFFKSAMPEGYVQERTIFFKDDGNYKTRAEVKFEGDTLVNRIELKG
IDFKEDGNILGHKLEYNYNSHNVYIMADKQKNGIKVNFKIRHNIEDGSVQLADHYQQNTPIGDG
PVLLPDNHYLSYQSALSKDPNEKRDHMVLLEFVTAAGITLGMDELYKAAAASGSGSGSENLYFQ
FHKSGAWKLPVSLVKGSGSGSGSGSSIAMEPPQHQHHHHQADQESGNNNNNKSGSGGYTCRQTS
TRWTPTTEQIKILKELYYNNAIRSPTADQIQKITARLRQFGKIEGKNVFYWFQNHKARERQKKR
FNGTNMTTPSSSPNSVMMAANDHYHPLLHHHHGVPMQRPANSVNVKLNQDHHLYHHNKPYPSFN
NGNLNHASSGTECGVVNASNGYMSSHVYGSMEQDCSMNYNNVGGGWANMDHHYSSAPYNFFDRA
KPLFGLEGHQEEEECGGDAYLEHRRTLPLFPMHGEDHINGGSGAIWKYGQSEVRPCASLELRLN Citrine-(SEQ ID NO: 43)
MVSKGEELFTGVVPILVELDGDVNGHKFSVSGEGEGDATYGKLTLKFICTTGKLPVPWPTLVTT
FGYGLMCFARYPDHMKQHDFFKSAMPEGYVQERTIFFKDDGNYKTRAEVKFEGDTLVNRIELKG
IDFKEDGNILGHKLEYNYNSHNVYIMADKQKNGIKVNFKIRHNIEDGSVQLADHYQQNTPIGDG
PVLLPDNHYLSYQSALSKDPNEKRDHMVLLEFVTAAGITLGMDELYK spacer-AAAASGSGSGS (SEQ ID NO: 44)

TEVsite-ENLYFQF (SEQ ID NO: 45)

Ndeg-HKSGAWKLPVSLVK (SEQ ID NO: 46)

spacer-GSGSGSGSGSSIA (SEQ ID NO: 47)

WUS-(SEQ ID NO: 48)
MEPPQHQHHHHQADQESGNNNNNKSGSGGYTCRQTSTRWTPTTEQIKILKELYYNNAIRSPTAD
QIQKITARLRQFGKIEGKNVFYWFQNHKARERQKKRFNGTNMTTPSSSPNSVMMAANDHYHPLL
HHHHGVPMQRPANSVNVKLNQDHHLYHHNKPYPSFNNGNLNHASSGTECGVVNASNGYMSSHVY
GSMEQDCSMNYNNVGGGWANMDHHYSSAPYNFFDRAKPLFGLEGHQEEEECGGDAYLEHRRTLP
LFPMHGEDHINGGSGAIWKYGQSEVRPCASLELRLN

C. TEV Protease and Degron Sequences to be Used
for TIPI Degron-Based CenH3 Depletion >CenH3_degron_DNA sequence_for_Arabidopsis:Citrine-spacer-
TEVsite-Ndeg-spacer-CenH3-stop (SEQ ID NO: 49)
ATGGTGAGCAAGGGCGAGGAGCTGTTCACCGGGGTGGTGCCCATCCTGGTCGAGCTGGACGGCG
ACGTAAACGGCCACAAGTTCAGCGTGTCCGGCGAGGGCGAGGGCGATGCCACCTACGGCAAGCT
GACCCTGAAGTTCATCTGCACCACCGGCAAGCTGCCCGTGCCCTGGCCCACCCTCGTGACCACC
TTCGGCTACGGCCTGATGTGCTTCGCCCGCTACCCCGACCACATGAAGCAGCACGACTTCTTCA
AGTCCGCCATGCCCGAAGGCTACGTCCAGGAGCGCACCATCTTCTTCAAGGACGGCAACTA
CAAGACCCGCGCCGAGGTGAAGTTCGAGGGCGACACCCTGGTGAACCGCATCGAGCTGAAGGGC
ATCGACTTCAAGGAGGACGGCAACATCCTGGGGCACAAGCTGGAGTACAACTACAACAGCCACA
ACGTCTATATCATGGCCGACAAGCAGAAGAACGGCATCAAGGTGAACTTCAAGATCCGCCACAA
CATCGAGGACGGCAGCGTGCAGCTCGCCGACCACTACCAGCAGAACACCCCCATCGGCGACGGC
CCCGTGCTGCTGCCCGACAACCACTACCTGAGCTACCAGTCCGCCCTGAGCAAGACCCCAACG
AGAAGCGCGATCACATGGTCCTGCTGGAGTTCGTGACCGCCGCCGGGATCACTCTCGGCATGGA
CGAGCTGTACAAGGCAGCGGCCGCTTCAGGGAGTGGTTCCGGAAGCGAAAACTTGTACTTCCAA
TTCCACAAGTCTGGTGCTTGGAAGTTGCCAGTTTCTTTGGTTAAGGGGAGTGGTTCCGGCAGCG
GCTCTGGATCGTCAATTGCTATGGCGAGAACCAAGCATCGCGTTACCAGGTCACAACCTCGGAA
TCAAACTGGTATCTTAAATCTGCTTTCTCTTTCAATTTTTACTTCTGATTTTACCCAGAATTTT
AGGTTTTTTATTTCGATTTGTTAACCCTAGATTTCGAATCTGAAATTTGTAGATGCCGCCGGT
GCTTCATCTTCTCAGGCGGCAGGTCCAACTACGGTACGGCATCTTTTTCCGTCTTAGGGTTTCC
AATGTTTCTTCCTTTTATCGTTATGATCAAATTTGTTTATCTATCGAAATTGAAGACCCCGACA
AGGAGAGGCGGTGAAGGTGGAGATAATACTCAACAAAGTGAGTTTTTTATATTTGAAGTCTTTT
TTTTCCCTCTTTTCATCTCTTTTGTTTGTGAAGTTATTCTTTTGTAACATCTGCAGCAAATCCT
ACAACTTCACCAGCTACTGGTACAAGGGTAAGATTTTTGTGACCATTGCTTATGAACTGCTTCA
ACTTTGATTTCGTTATTAAGCTGACAAAATTCTCGTTTTGGTTTGTCAAGAGAGGGGCTAAGAG
ATCCAGACAGGCTATGCCACGAGGTTTGTTTAAAAAAAAAACCAATCTCTTGTGATATCCCTG
AGAATACAGGACACTTAGTGTGTTTAAAACTAATCTTCGGTGTTGTCCTTGTAGGCTCACAGAA
GAAGTCTTATCGATACAGGCCAGGAACCGTTGCTCTAAAAGAGATTCGCCATTTCCAGAAGCAG
ACAAACCTTCTTATTCCGGCTGCCAGTTTCATAAGAGAAGTTAGTTACTCTTTTTCTTACCAGC
CATAATAAGTTTCACAGCTTAACAATATTCATATATACTAACAGAGGCACAAGCCTTTTGGTGT
TTAATGTGGCTAGTTTTAGGATTTGCACACCCCACACATATCTGAGCATCAATGCAGTGTACAT
AGTGAGTGATATAGCAATTTAACTAAAATTCAGAGTAATCGTGAGGCCAACCCTCCTTGTTTAA
GGAGTGTGTAATCTAGTTTGTCTTTGAGGTTATGAGCTCATAGATTCAGAACCATATGATTCCT
GTAGCTACAAAACTCAACATGAATCGTCAGTGATGTGGAAATGCTGATTTGTGTTACAAACAAA
CTATTTTACATTGTTTTTCCAGGTGAGAAGTATAACCCATATGTTGGCCCCTCCCCAAATCAAT
CGTTGGACAGCTGAAGCTCTTGTTGCTCTTCAAGAGGTACCAATCCTTCAACTTTTTCTTTATA
CGAATGTATGAATATAGATATAGAGATAGTCACACATTTCAACTAATGTCATTCCCCTTGATGA
CCAATCAACCTAATCACACAAATTCTTTGTGGTAGGCGGCAGAAGATTACTTGGTTGGTTTGTT
CTCAGATTCAATGCTCTGTGCTATCCATGCAAGACGTGTTACTCTAAGTAAGTACTCTAAAAGA -continued

```
AGACATTTTTCAGTCTCAACTTAGGAATCACAAGCATACATTTTATATCCCTTTGAATCATTAG
TTACTTGAATATCATATATAAAAATGCTTATCTATATCTGTTTTTTGTTCATATCAGTGAGAAA
AGACTTTGAACTTGCACGCCGGCTTGGAGGAAAAGGCAGACCATGGTGA

Citrine-(SEQ ID NO: 50)
ATGGTGAGCAAGGGCGAGGAGCTGTTCACCGGGGTGGTGCCCATCCTGGTCGAGCTGGACGGCG
ACGTAAACGGCCACAAGTTCAGCGTGTCCGGCGAGGGCGAGGGCGATGCCACCTACGGCAAGCT
GACCCTGAAGTTCATCTGCACCACCGGCAAGCTGCCCGTGCCCTGGCCCACCCTCGTGACCACC
TTCGGCTACGGCCTGATGTGCTTCGCCCGCTACCCCGACCACATGAAGCAGCACGACTTCTTCA
AGTCCGCCATGCCCGAAGGCTACGTCCAGGAGCGCACCATCTTCTTCAAGGACGACGGCAACTA
CAAGACCCGCGCCGAGGTGAAGTTCGAGGGCGACACCCTGGTGAACCGCATCGAGCTGAAGGGC
ATCGACTTCAAGGAGGACGGCAACATCCTGGGGCACAAGCTGGAGTACAACTACAACAGCCACA
ACGTCTATATCATGGCCGACAAGCAGAAGAACGGCATCAAGGTGAACTTCAAGATCCGCCACAA
CATCGAGGACGGCAGCGTGCAGCTCGCCGACCACTACCAGCAGAACACCCCCATCGGCGACGGC
CCCGTGCTGCTGCCCGACAACCACTACCTGAGCTACCAGTCCGCCCTGAGCAAAGACCCCAACG
AGAAGCGCGATCACATGGTCCTGCTGGAGTTCGTGACCGCCGCCGGGATCACTCTCGGCATGGA
CGAGCTGTACAAG spacer-GCAGCGGCCGCTTCAGGGAGTGGTTCCGGAAGC (SEQ ID NO: 51)

TEVsite-GAAAACTTGTACTTCCAATTC (SEQ ID NO: 52)

Ndeg-CACAAGTCTGGTGCTTGGAAGTTGCCAGTTTCTTTGGTTAAG (SEQ ID
NO: 53)

spacerGGGAGTGGTTCCGGCAGCGGCTCTGGATCGTCAATTGCT (SEQ ID NO: 54)

CenH3-(SEQ ID NO: 55)
ATGGCGAGAACCAAGCATCGCGTTACCAGGTCACAACCTCGGAATCAAACTGGTATCTTAAATC
TGCTTTCTCTTTCAATTTTTACTTCTGATTTTACCCAGAATTTTAGGTTTTTTATTTCGATTTT
GTTAACCCTAGATTTCGAATCTGAAATTTGTAGATGCCGCCGGTGCTTCATCTTCTCAGGCGGC
AGGTCCAACTACGGTACGGCATCTTTTTCCGTCTTAGGGTTTCCAATGTTTCTTCCTTTTATCG
TTATGATCAAATTTGTTTATCTATCGAAATTGAAGACCCCGACAAGGAGAGGCGGTGAAGGTGG
AGATAATACTCAACAAAGTGAGTTTTTTATATTTGAAGTCTTTTTTTTCCCTCTTTTCATCTCT
TTTGTTTGTGAAGTTATTCTTTTGTAACATCTGCAGCAAATCCTACAACTTCACCAGCTACTGG
TACAAGGGTAAGATTTTTGTGACCATTGCTTATGAACTGCTTCAACTTTGATTTCGTTATTAAG
CTGACAAAATTCTCGTTTTGGTTTGTCAAGAGAGGGGCTAAGAGATCCAGACAGGCTATGCCAC
GAGGTTTGTTTTAAAAAAAAAACCAATCTCTTGTGATATCCCTGAGAATACAGGACACTTAGTG
TGTTTAAAACTAATCTTCGGTGTTGTCCTTGTAGGCTCACAGAAGAAGTCTTATCGATACAGGC
CAGGAACCGTTGCTCTAAAAGAGATTCGCCATTTCCAGAAGCAGACAAACCTTCTTATTCCGGC
TGCCAGTTTCATAAGAGAAGTTAGTTACTCTTTTTCTTACCAGCCATAATAAGTTTCACAGCTT
AACAATATTCATATATACTAACAGAGGCACAAGCCTTTTGGTGTTTAATGTGGCTAGTTTTAGG
ATTTGCACACCCCACACATATCTGAGCATCAATGCAGTGTACATAGTGAGTGATATAGCAATTT
AACTAAAATTCAGAGTAATCGTGAGGCCAACCCTCCTTGTTTAAGGAGTGTGTAATCTAGTTTG
TCTTTGAGGTTATGAGCTCATAGATTCAGAACCATATGATTCCTGTAGCTACAAAACTCAACAT
GAATCGTCAGTGATGTGGAAATGCTGATTTGTGTTACAAACAAACTATTTTACATTGTTTTTCC
AGGTGAGAAGTATAACCCATATGTTGGCCCCTCCCCAAATCAATCGTTGGACAGCTGAAGCTCT
TGTTGCTCTTCAAGAGGTACCAATCCTTCAACTTTTTCTTTATACGAATGTATGAATATAGATA
TAGAGATAGTCACACATTTCAACTAATGTCATTCCCCTTGATGACCAATCAACCTAATCACACA
AATTCTTTGTGGTAGGCGGCAGAAGATTACTTGGTTGGTTTGTTCTCAGATTCAATGCTCTGTG
CTATCCATGCAAGACGTGTTACTCTAAGTAAGTACTCTAAAAGAAGACATTTTTCAGTCTCAAC
TTAGGAATCACAAGCATACATTTTATATCCCTTTGAATCATTAGTTACTTGAATATCATATATA
AAAATGCTTATCTATATCTGTTTTTTGTTCATATCAGTGAGAAAAGACTTTGAACTTGCACGCC
GGCTTGGAGGAAAAGGCAGACCATGG
Stop-TGA
```

LITERATURE CITED

Daum, G., Medzihradszky, A., Suzaki, T., & Lohmann, J. U. (2014). A mechanistic framework for noncell autonomous stem cell induction in Arabidopsis. Proc Natl Acad Sci USA, 111(40), 14619-14624. doi: 10.1073/pnas.1406446111

Kim, J., Ishiguro, K., Nambu, A., Akiyoshi, B., Yokobayashi, S., Kagami, A., ... Watanabe, Y. (2015). Meikin is a conserved regulator of meiosis-I-specific kinetochore function. Nature, 517(7535), 466-471. doi: 10.1038/nature14097

Ravi, M., & Chan, S. W. (2010). Haploid plants produced by centromere-mediated genome elimination. Nature, 464 (7288), 615-618. doi: 10.1038/nature08842

Raychaudhuri, N., Dubruille, R., Orsi, G. A., Bagheri, H. C., Loppin, B., and Lehner, C. F. (2012). Transgenerational Propagation and Quantitative Maintenance of Paternal Centromeres Depends on Cid/Cenp-A Presence in *Drosophila* Sperm. Plos Biol 10

Taxis, C., Stier, G., Spadaccini, R., & Knop, M. (2009). Efficient protein depletion by genetically controlled deprotection of a dormant N-degron. Mol Syst Biol, 5, 267. doi: 10.1038/msb.2009.25.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of targeting a kinetochore protein for degradation, the method comprising:
 a. introducing into a gamete cell of a parent plant a polypeptide comprising a peptide sequence linked to a protease cleavage site linked to N-degron linked to a kinetochore protein, wherein the peptide sequence is of sufficient length to block the polypeptide in an N-degron-dependent manner, and wherein the kinetochore protein is CENH3, and;
 b. introducing into the gamete cell of a parent plant a protease that targets the protease cleavage site, thereby releasing the peptide sequence such that the N-degron is at the amino terminus of the polypeptide, thereby targeting the polypeptide for degradation.

2. The method of claim 1, wherein one or two alleles of the endogenous kinetochore protein coding sequence of the plant is inactivated or knocked out.

3. The method of claim 1, wherein the protease is a tobacco etch virus (TEV) protease.

4. The method of claim 1, wherein the introducing in step a comprises expressing the polypeptide from an expression cassette comprising a promoter operably linked to a sequence encoding the polypeptide.

5. The method of claim 4, wherein the promoter is a kinetochore protein gene promoter.

6. The method of claim 1, wherein the introducing in step b comprises expressing the polypeptide from an expression cassette comprising a heterologous promoter specific for a gamete lineage operably linked to a sequence encoding the protease.

7. The method of claim 6, wherein the promoter specific for a gamete lineage is specific for a central cell, egg cell, or sperm cell.

8. The method of claim 1, further comprising generating selfed progeny from the plant and selecting progeny from the plant having half the chromosomes of the plant.

9. The method of claim 8, wherein the selected progeny are haploid.

10. The method of claim 9, further comprising generating doubled haploid plants from the haploid progeny.

11. A plant comprising:
a first expression cassette comprising a promoter operably linked to a polynucleotide encoding a polypeptide comprising a peptide sequence linked to a protease cleavage site linked to N-degron linked to a kinetochore protein, wherein the peptide sequence is of sufficient length to block the polypeptide in an N-degron-dependent manner and wherein the kinetochore protein is CENH3, and
a second expression cassette comprising a heterologous promoter linked to a second polynucleotide encoding the protease, wherein the heterologous promoter is specific for a gamete lineage.

12. The plant of claim 11, wherein the promoter specific for a gamete lineage is specific for a central cell, egg cell, or sperm cell.

13. An expression cassette comprising a promoter operably linked to a polynucleotide encoding a polypeptide comprising a peptide sequence linked to a protease cleavage site linked to N-degron linked to a kinetochore protein, wherein the kinetochore protein is CENH3.

* * * * *

SEQUENCE LISTING

<160> NUMBER OF SEQ ID NOS: 55

<210> SEQ ID NO 1
<211> LENGTH: 1149
<212> TYPE: DNA
<213> ORGANISM: Artificial Sequence
<220> FEATURE:
<223> OTHER INFORMATION: synthetic TEV protease DNA sequence for yeast:P14-myc-TEV234-stop

<400> SEQUENCE: 1

```
atggcgatgc aagcggccaa gagggcgaac attcgtcttc cacctgaagt aaatagaata      60
ttgtatataa gaaatttgcc atacaaaatc acagctgaag aaatgtatga tatatttggg     120
aaatatggac ctattcgtca aatcagagtg gggaacacac ctgaaactag aggaacagct     180
tatgtggtct atgaggacat ctttgatgcc aagaatgcat gtgatcacct atcgggattc     240
aatgttgta acagatacct tgtggttttg tactataatg ccaacagggc atttcagaag     300
atggacacaa agaagaagga ggaacagttg aagcttttga aggagaaata tggcatcaac     360
acatatcctc caagatgga acaaaagttg atatctgaag aagacttgcc catgagcggc     420
ctggtgccga gaggcagcgc catgggagaa agcttgttta agggaccacg tgattacaac     480
ccgatatcga gcgacatttg tcatttgacg aatgaatctg atgggcacac aacatcgttg     540
tatggtattg gatttggtcc cttcatcatt acaaacaagc acttgtttcg tagaaataat     600
ggaacactgt tggtccaatc actacatggt gtattcaagg tcaaggacac cacgactttg     660
caacaacact tggttgatgg gagggacatg atgattatta gaatgcctaa ggatttccca     720
ccatttcctc aaaagctgaa atttagagag ccacaagggg aagagagaat atgtcttgtg     780
acaaccaact ccaagctaa gagcatgtct agcatggtgt cagacactag ttgcacattc     840
ccttcatctg atggtatatt ctggaagcat tggattcaaa ccaaggatgg gcagtgtggc     900
agtccattag tatcaactag agatgggttc attgttggta tacactcagc atcgaatttc     960
accaacacaa acaattattt cacaagcgtg ccgaaaaact tcatggaatt gttgacaaat    1020
caggaggcgc agcagtgggt tagtggttgg agattaaacg ctgactcagt attgtggggg    1080
ggccataaag ttttcatggt taaacctgaa gaacctttc agccagttaa ggaagcgact    1140
caattgtaa                                                             1149
```

<210> SEQ ID NO 2
<211> LENGTH: 375
<212> TYPE: DNA
<213> ORGANISM: Artificial Sequence
<220> FEATURE:
<223> OTHER INFORMATION: synthetic P14 DNA sequence

<400> SEQUENCE: 2

```
atggcgatgc aagcggccaa gagggcgaac attcgtcttc cacctgaagt aaatagaata      60
ttgtatataa gaaatttgcc atacaaaatc acagctgaag aaatgtatga tatatttggg     120
aaatatggac ctattcgtca aatcagagtg gggaacacac ctgaaactag aggaacagct     180
tatgtggtct atgaggacat ctttgatgcc aagaatgcat gtgatcacct atcgggattc     240
aatgttgta acagatacct tgtggttttg tactataatg ccaacagggc atttcagaag     300
atggacacaa agaagaagga ggaacagttg aagcttttga aggagaaata tggcatcaac     360
acatatcctc caag                                                       375
```

<210> SEQ ID NO 3

<211> LENGTH: 66
<212> TYPE: DNA
<213> ORGANISM: Artificial Sequence
<220> FEATURE:
<223> OTHER INFORMATION: synthetic myc DNA sequence

<400> SEQUENCE: 3

```
atggaacaaa agttgatatc tgaagaagac ttgcccatga gcggcctggt gccgagaggc    60
agcgcc                                                                66
```

<210> SEQ ID NO 4
<211> LENGTH: 705
<212> TYPE: DNA
<213> ORGANISM: Artificial Sequence
<220> FEATURE:
<223> OTHER INFORMATION: synthetic TEV234 DNA sequence

<400> SEQUENCE: 4

```
atgggagaaa gcttgtttaa gggaccacgt gattacaacc cgatatcgag cgacatttgt    60
catttgacga atgaatctga tgggcacaca acatcgttgt atggtattgg atttggtccc   120
ttcatcatta caaacaagca cttgtttcgt agaaataatg gaacactgtt ggtccaatca   180
ctacatggtg tattcaaggt caaggacacc acgactttgc aacaacactt ggttgatggg   240
agggacatga tgattattag aatgcctaag gatttcccac catttcctca aaagctgaaa   300
tttagagagc cacaaaggga agagagaata tgtcttgtga caaccaactt ccaagctaag   360
agcatgtcta gcatggtgtc agacactagt tgcacattcc cttcatctga tggtatattc   420
tggaagcatt ggattcaaac caaggatggg cagtgtggca gtccattagt atcaactaga   480
gatgggttca ttgttggtat acactcagca tcgaatttca ccaacacaaa caattatttc   540
acaagcgtgc cgaaaaactt catggaattg ttgacaaatc aggaggcgca gcagtggggtt   600
agtggttgga gattaaacgc tgactcagta ttgtgggggg ccataaagt tttcatggtt   660
aaacctgaag aacctttttca gccagttaag gaagcgactc aattg                   705
```

<210> SEQ ID NO 5
<211> LENGTH: 382
<212> TYPE: PRT
<213> ORGANISM: Artificial Sequence
<220> FEATURE:
<223> OTHER INFORMATION: synthetic TEV protease protein sequence for
      yeast:P14-myc-TEV234-stop

<400> SEQUENCE: 5

```
Met Ala Met Gln Ala Ala Lys Arg Ala Asn Ile Arg Leu Pro Pro Glu
1               5                   10                  15

Val Asn Arg Ile Leu Tyr Ile Arg Asn Leu Pro Tyr Lys Ile Thr Ala
            20                  25                  30

Glu Glu Met Tyr Asp Ile Phe Gly Lys Tyr Gly Pro Ile Arg Gln Ile
        35                  40                  45

Arg Val Gly Asn Thr Pro Glu Thr Arg Gly Thr Ala Tyr Val Val Tyr
    50                  55                  60

Glu Asp Ile Phe Asp Ala Lys Asn Ala Cys Asp His Leu Ser Gly Phe
65                  70                  75                  80

Asn Val Cys Asn Arg Tyr Leu Val Val Leu Tyr Asn Ala Asn Arg
                85                  90                  95

Ala Phe Gln Lys Met Asp Thr Lys Lys Lys Glu Glu Gln Leu Lys Leu
            100                 105                 110

Leu Lys Glu Lys Tyr Gly Ile Asn Thr Tyr Pro Pro Lys Met Glu Gln
```

```
              115                 120                 125
Lys Leu Ile Ser Glu Glu Asp Leu Pro Met Ser Gly Leu Val Pro Arg
        130                 135                 140

Gly Ser Ala Met Gly Glu Ser Leu Phe Lys Gly Pro Arg Asp Tyr Asn
145                 150                 155                 160

Pro Ile Ser Ser Asp Ile Cys His Leu Thr Asn Glu Ser Asp Gly His
                165                 170                 175

Thr Thr Ser Leu Tyr Gly Ile Gly Phe Gly Pro Phe Ile Ile Thr Asn
            180                 185                 190

Lys His Leu Phe Arg Arg Asn Asn Gly Thr Leu Leu Val Gln Ser Leu
        195                 200                 205

His Gly Val Phe Lys Val Lys Asp Thr Thr Thr Leu Gln Gln His Leu
    210                 215                 220

Val Asp Gly Arg Asp Met Met Ile Ile Arg Met Pro Lys Asp Phe Pro
225                 230                 235                 240

Pro Phe Pro Gln Lys Leu Lys Phe Arg Glu Pro Gln Arg Glu Glu Arg
                245                 250                 255

Ile Cys Leu Val Thr Thr Asn Phe Gln Ala Lys Ser Met Ser Ser Met
            260                 265                 270

Val Ser Asp Thr Ser Cys Thr Phe Pro Ser Ser Asp Gly Ile Phe Trp
        275                 280                 285

Lys His Trp Ile Gln Thr Lys Asp Gly Gln Cys Gly Ser Pro Leu Val
    290                 295                 300

Ser Thr Arg Asp Gly Phe Ile Val Gly Ile His Ser Ala Ser Asn Phe
305                 310                 315                 320

Thr Asn Thr Asn Asn Tyr Phe Thr Ser Val Pro Lys Asn Phe Met Glu
                325                 330                 335

Leu Leu Thr Asn Gln Glu Ala Gln Gln Trp Val Ser Gly Trp Arg Leu
            340                 345                 350

Asn Ala Asp Ser Val Leu Trp Gly Gly His Lys Val Phe Met Val Lys
        355                 360                 365

Pro Glu Glu Pro Phe Gln Pro Val Lys Glu Ala Thr Gln Leu
    370                 375                 380

<210> SEQ ID NO 6
<211> LENGTH: 125
<212> TYPE: PRT
<213> ORGANISM: Artificial Sequence
<220> FEATURE:
<223> OTHER INFORMATION: synthetic P14 protein sequence

<400> SEQUENCE: 6

Met Ala Met Gln Ala Ala Lys Arg Ala Asn Ile Arg Leu Pro Pro Glu
1               5                   10                  15

Val Asn Arg Ile Leu Tyr Ile Arg Asn Leu Pro Tyr Lys Ile Thr Ala
            20                  25                  30

Glu Glu Met Tyr Asp Ile Phe Gly Lys Tyr Gly Pro Ile Arg Gln Ile
        35                  40                  45

Arg Val Gly Asn Thr Pro Glu Thr Arg Gly Thr Ala Tyr Val Val Tyr
    50                  55                  60

Glu Asp Ile Phe Asp Ala Lys Asn Ala Cys Asp His Leu Ser Gly Phe
65                  70                  75                  80

Asn Val Cys Asn Arg Tyr Leu Val Val Leu Tyr Tyr Asn Ala Asn Arg
                85                  90                  95

Ala Phe Gln Lys Met Asp Thr Lys Lys Lys Glu Glu Gln Leu Lys Leu
```

```
                    100                 105                 110
Leu Lys Glu Lys Tyr Gly Ile Asn Thr Tyr Pro Pro Lys
        115                 120                 125

<210> SEQ ID NO 7
<211> LENGTH: 22
<212> TYPE: PRT
<213> ORGANISM: Artificial Sequence
<220> FEATURE:
<223> OTHER INFORMATION: synthetic myc protein sequence

<400> SEQUENCE: 7

Met Glu Gln Lys Leu Ile Ser Glu Glu Asp Leu Pro Met Ser Gly Leu
1               5                   10                  15

Val Pro Arg Gly Ser Ala
            20

<210> SEQ ID NO 8
<211> LENGTH: 235
<212> TYPE: PRT
<213> ORGANISM: Artificial Sequence
<220> FEATURE:
<223> OTHER INFORMATION: synthetic TEV234 protein sequence

<400> SEQUENCE: 8

Met Gly Glu Ser Leu Phe Lys Gly Pro Arg Asp Tyr Asn Pro Ile Ser
1               5                   10                  15

Ser Asp Ile Cys His Leu Thr Asn Glu Ser Asp Gly His Thr Thr Ser
            20                  25                  30

Leu Tyr Gly Ile Gly Phe Gly Pro Phe Ile Ile Thr Asn Lys His Leu
        35                  40                  45

Phe Arg Arg Asn Asn Gly Thr Leu Leu Val Gln Ser Leu His Gly Val
    50                  55                  60

Phe Lys Val Lys Asp Thr Thr Thr Leu Gln Gln His Leu Val Asp Gly
65                  70                  75                  80

Arg Asp Met Met Ile Ile Arg Met Pro Lys Asp Phe Pro Pro Phe Pro
                85                  90                  95

Gln Lys Leu Lys Phe Arg Glu Pro Gln Arg Glu Glu Arg Ile Cys Leu
            100                 105                 110

Val Thr Thr Asn Phe Gln Ala Lys Ser Met Ser Ser Met Val Ser Asp
        115                 120                 125

Thr Ser Cys Thr Phe Pro Ser Ser Asp Gly Ile Phe Trp Lys His Trp
    130                 135                 140

Ile Gln Thr Lys Asp Gly Gln Cys Gly Ser Pro Leu Val Ser Thr Arg
145                 150                 155                 160

Asp Gly Phe Ile Val Gly Ile His Ser Ala Ser Asn Phe Thr Asn Thr
                165                 170                 175

Asn Asn Tyr Phe Thr Ser Val Pro Lys Asn Phe Met Glu Leu Leu Thr
            180                 185                 190

Asn Gln Glu Ala Gln Gln Trp Val Ser Gly Trp Arg Leu Asn Ala Asp
        195                 200                 205

Ser Val Leu Trp Gly Gly His Lys Val Phe Met Val Lys Pro Glu Glu
    210                 215                 220

Pro Phe Gln Pro Val Lys Glu Ala Thr Gln Leu
225                 230                 235

<210> SEQ ID NO 9
<211> LENGTH: 1758
```

```
<212> TYPE: DNA
<213> ORGANISM: Artificial Sequence
<220> FEATURE:
<223> OTHER INFORMATION: synthetic Degron construct DNA sequence for
      yeast:GFP cODC1 spacer TEVrec Ndegron spacer SF3b spacer mKATE
      stop

<400> SEQUENCE: 9
atgtctaaag gtgaagaatt attcactggt gttgtcccaa ttttggttga attagatggt      60
gatgttaatg gtcacaaatt ttctgtctcc ggtgaaggtg aaggtgatgc tacttacggt     120
aaattgacct taaaatttat ttgtactact ggtaaattgc cagttccatg gccaacctta     180
gtcactactt tcggttatgg tgttcaatgt tttgcgagat acccagatca tatgaaacaa     240
catgactttt tcaagtctgc catgccagaa ggttatgttc aagaagaac tatttttttc      300
aaagatgacg gtaactacaa gaccagagct gaagtcaagt ttgaaggtga taccttagtt     360
aatagaatcg aattaaaagg tattgatttt aaagaagatg gtaacatttt aggtcacaaa     420
ttggaataca actataactc tcacaatgtt tacatcatgg ctgacaaaca aaagaatggt     480
atcaaagtta acttcaaaat tagacacaac attgaagatg gttctgttca attagctgac     540
cattatcaac aaaatactcc aattggtgat ggtccagtct tgttaccaga caaccattac     600
ttatccactc aatctgcctt atccaaagat ccaaacgaaa agagagacca catggtcttg     660
ttagaatttg ttactgctgc tggtattacc catggtatgg atgaattgta caaattgcca     720
atgtcttgtg cacaagaatc tattacttct ttgtacaaga aggctggttc tgaaaacttg     780
tacttccaat tccacaagtc tggtgcttgg aagttgccag tttctttggt taagagaggg     840
atcgataagc ttgattataa agaacagctt caggcttggc ggtgggaaag agaaattgat     900
gagagaaatc gcccactttc tgatgaggaa ttagatgcta tgttcccaga aggatataag     960
gtacttcctc ctccagctgg ttatgttcct attcgaactc cagctcatat ggatcgaatt    1020
cctgcagtag caggtgctgg tgctggtgct ggagcaatgt ctgaattaat taagaaaaat    1080
atgcatatga attatatat ggaaggtaca gttaataatc atcatttaa atgtacatct      1140
gaaggtgaag gtaaaccata tgaaggtaca caaacaatga gaattaaagt tgttgaaggt    1200
ggtccattac catttgcttt tgatattta gctacatctt tatgtatgg ttctaagaca       1260
tttattaatc atacacaagg tattccagat tttttttaaac aatctttcc agaaggtttt    1320
acatgggaaa gagttacaac atatgaagat ggtggtgttt taacagctac acaagataca    1380
tctttacaag atggttgttt aatttataat gttaaaatta gaggtgttaa ttttccatct    1440
aatggtccag ttatgcaaaa aaaaacatta ggttgggaag cttctacaga aatgttatat    1500
ccagctgatg gtggtttaga aggtaggtct gatatggctt taaaattagt tggtggtggt    1560
catttaattt gtaatttgaa aacaacatat aggtctaaaa aaccagctaa aaatttaaaa    1620
atgccaggtg tttattatgt tgatagaaga ttagaaagaa ttaagaagc tgataaagaa     1680
acatatgttg aacaacatga agttgctgtt gctagatatt gtgatttacc atctaaatta    1740
ggtcataaag gatcctaa                                                  1758

<210> SEQ ID NO 10
<211> LENGTH: 714
<212> TYPE: DNA
<213> ORGANISM: Artificial Sequence
<220> FEATURE:
<223> OTHER INFORMATION: synthetic GFP DNA sequence

<400> SEQUENCE: 10
```

```
atgtctaaag gtgaagaatt attcactggt gttgtcccaa ttttggttga attagatggt    60
gatgttaatg gtcacaaatt ttctgtctcc ggtgaaggtg aaggtgatgc tacttacggt   120
aaattgacct taaaatttat tgtactact ggtaaattgc cagttccatg gccaacctta    180
gtcactactt tcggttatgg tgttcaatgt tttgcgagat acccagatca tatgaaacaa    240
catgactttt tcaagtctgc catgccagaa ggttatgttc aagaaagaac tatttttttc    300
aaagatgacg gtaactacaa gaccagagct gaagtcaagt ttgaaggtga taccttagtt    360
aatagaatcg aattaaaagg tattgatttt aagaagatg gtaacatttt aggtcacaaa    420
ttggaataca actataactc tcacaatgtt tacatcatgg ctgacaaaca aaagaatggt    480
atcaaagtta acttcaaaat tagacacaac attgaagatg gttctgttca attagctgac    540
cattatcaac aaaatactcc aattggtgat ggtccagtct tgttaccaga caaccattac    600
ttatccactc aatctgcctt atccaaagat ccaaacgaaa agagagacca catggtcttg    660
ttagaatttg ttactgctgc tggtattacc catggtatgg atgaattgta caaa           714

<210> SEQ ID NO 11
<211> LENGTH: 24
<212> TYPE: DNA
<213> ORGANISM: Artificial Sequence
<220> FEATURE:
<223> OTHER INFORMATION: synthetic cODC1 DNA sequence

<400> SEQUENCE: 11
ttgccaatgt cttgtgcaca agaa                                           24

<210> SEQ ID NO 12
<211> LENGTH: 33
<212> TYPE: DNA
<213> ORGANISM: Artificial Sequence
<220> FEATURE:
<223> OTHER INFORMATION: synthetic spacer DNA sequence

<400> SEQUENCE: 12
tctattactt ctttgtacaa gaaggctggt tct                                 33

<210> SEQ ID NO 13
<211> LENGTH: 21
<212> TYPE: DNA
<213> ORGANISM: Artificial Sequence
<220> FEATURE:
<223> OTHER INFORMATION: synthetic TEVrec DNA sequence

<400> SEQUENCE: 13
gaaaacttgt acttccaatt c                                              21

<210> SEQ ID NO 14
<211> LENGTH: 42
<212> TYPE: DNA
<213> ORGANISM: Artificial Sequence
<220> FEATURE:
<223> OTHER INFORMATION: synthetic Ndegron DNA sequence

<400> SEQUENCE: 14
cacaagtctg gtgcttggaa gttgccagtt tctttggtta ag                       42

<210> SEQ ID NO 15
<211> LENGTH: 27
<212> TYPE: DNA
<213> ORGANISM: Artificial Sequence
<220> FEATURE:
<223> OTHER INFORMATION: synthetic spacer DNA sequence
```

<400> SEQUENCE: 15
agagggatcg ataagcttga ttataaa                                          27

<210> SEQ ID NO 16
<211> LENGTH: 144
<212> TYPE: DNA
<213> ORGANISM: Artificial Sequence
<220> FEATURE:
<223> OTHER INFORMATION: synthetic SF3b DNA sequence

<400> SEQUENCE: 16
gaacagcttc aggcttggcg gtgggaaaga gaaattgatg agagaaatcg cccactttct      60
gatgaggaat tagatgctat gttcccagaa ggatataagg tacttcctcc tccagctggt     120
tatgttccta ttcgaactcc agct                                            144

<210> SEQ ID NO 17
<211> LENGTH: 24
<212> TYPE: DNA
<213> ORGANISM: Artificial Sequence
<220> FEATURE:
<223> OTHER INFORMATION: synthetic spacer DNA sequence

<400> SEQUENCE: 17
catatggatc gaattcctgc agta                                             24

<210> SEQ ID NO 18
<211> LENGTH: 726
<212> TYPE: DNA
<213> ORGANISM: Artificial Sequence
<220> FEATURE:
<223> OTHER INFORMATION: synthetic TEV234 DNA sequence

<400> SEQUENCE: 18
gcaggtgctg gtgctggtgc tggagcaatg tctgaattaa ttaaagaaaa tatgcatatg      60
aaattatata tggaaggtac agttaataat catcatttta aatgtacatc tgaaggtgaa     120
ggtaaaccat atgaaggtac acaaacaatg agaattaaag ttgttgaagg tggtccatta     180
ccatttgctt ttgatatttt agctacatct tttatgtatg gttctaagac atttattaat     240
catacacaag gtattccaga tttttttaaa caatcttttc cagaaggttt tacatgggaa     300
agagttacaa catatgaaga tggtggtgtt ttaacagcta cacaagatac atctttacaa     360
gatggttgtt aatttataa tgttaaaatt agaggtgtta attttccatc taatggtcca     420
gttatgcaaa aaaaaacatt aggttgggaa gcttctacag aaatgttata tccagctgat     480
ggtggtttag aaggtaggtc tgatatggct ttaaaattag ttggtggtgg tcatttaatt     540
tgtaatttga aaacaacata taggtctaaa aaaccagcta aaaatttaaa aatgccaggt     600
gtttattatg ttgatagaag attagaaaga attaagaag ctgataaaga aacatatgtt      660
gaacaacatg aagttgctgt tgctagatat tgtgatttac catctaaatt aggtcataaa     720
ggatcc                                                                726

<210> SEQ ID NO 19
<211> LENGTH: 585
<212> TYPE: PRT
<213> ORGANISM: Artificial Sequence
<220> FEATURE:
<223> OTHER INFORMATION: synthetic Degron protein DNA sequence for
      yeast:GFP cODC1 spacer TEVrec Ndegron spacer SF3b spacer mKATE
      stop

<400> SEQUENCE: 19

```
Met Ser Lys Gly Glu Glu Leu Phe Thr Gly Val Val Pro Ile Leu Val
  1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
 50                  55                  60

Gly Tyr Gly Val Gln Cys Phe Ala Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Leu Pro
225                 230                 235                 240

Met Ser Cys Ala Gln Glu Ser Ile Thr Ser Leu Tyr Lys Lys Ala Gly
                245                 250                 255

Ser Glu Asn Leu Tyr Phe Gln Phe His Lys Ser Gly Ala Trp Lys Leu
            260                 265                 270

Pro Val Ser Leu Val Lys Arg Gly Ile Asp Lys Leu Asp Tyr Lys Glu
        275                 280                 285

Gln Leu Gln Ala Trp Arg Trp Glu Arg Glu Ile Asp Glu Arg Asn Arg
    290                 295                 300

Pro Leu Ser Asp Glu Glu Leu Asp Ala Met Phe Pro Glu Gly Tyr Lys
305                 310                 315                 320

Val Leu Pro Pro Pro Ala Gly Tyr Val Pro Ile Arg Thr Pro Ala His
                325                 330                 335

Met Asp Arg Ile Pro Ala Val Ala Gly Ala Gly Ala Gly Ala
            340                 345                 350

Met Ser Glu Leu Ile Lys Glu Asn Met His Met Lys Leu Tyr Met Glu
        355                 360                 365

Gly Thr Val Asn Asn His His Phe Lys Cys Thr Ser Glu Gly Glu Gly
    370                 375                 380

Lys Pro Tyr Glu Gly Thr Gln Thr Met Arg Ile Lys Val Val Glu Gly
385                 390                 395                 400

Gly Pro Leu Pro Phe Ala Phe Asp Ile Leu Ala Thr Ser Phe Met Tyr
                405                 410                 415
```

```
Gly Ser Lys Thr Phe Ile Asn His Thr Gln Gly Ile Pro Asp Phe Phe
            420                 425                 430

Lys Gln Ser Phe Pro Glu Gly Phe Thr Trp Glu Arg Val Thr Thr Tyr
        435                 440                 445

Glu Asp Gly Gly Val Leu Thr Ala Thr Gln Asp Thr Ser Leu Gln Asp
    450                 455                 460

Gly Cys Leu Ile Tyr Asn Val Lys Ile Arg Gly Val Asn Phe Pro Ser
465                 470                 475                 480

Asn Gly Pro Val Met Gln Lys Lys Thr Leu Gly Trp Glu Ala Ser Thr
                485                 490                 495

Glu Met Leu Tyr Pro Ala Asp Gly Gly Leu Glu Gly Arg Ser Asp Met
            500                 505                 510

Ala Leu Lys Leu Val Gly Gly Gly His Leu Ile Cys Asn Leu Lys Thr
        515                 520                 525

Thr Tyr Arg Ser Lys Lys Pro Ala Lys Asn Leu Lys Met Pro Gly Val
    530                 535                 540

Tyr Tyr Val Asp Arg Arg Leu Glu Arg Ile Lys Glu Ala Asp Lys Glu
545                 550                 555                 560

Thr Tyr Val Glu Gln His Glu Val Ala Val Ala Arg Tyr Cys Asp Leu
                565                 570                 575

Pro Ser Lys Leu Gly His Lys Gly Ser
            580                 585

<210> SEQ ID NO 20
<211> LENGTH: 238
<212> TYPE: PRT
<213> ORGANISM: Artificial Sequence
<220> FEATURE:
<223> OTHER INFORMATION: synthetic GFP protein sequence

<400> SEQUENCE: 20

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190
```

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 21
<211> LENGTH: 8
<212> TYPE: PRT
<213> ORGANISM: Artificial Sequence
<220> FEATURE:
<223> OTHER INFORMATION: synthetic cODC1 protein sequence

<400> SEQUENCE: 21

Leu Pro Met Ser Cys Ala Gln Glu
1               5

<210> SEQ ID NO 22
<211> LENGTH: 11
<212> TYPE: PRT
<213> ORGANISM: Artificial Sequence
<220> FEATURE:
<223> OTHER INFORMATION: synthetic spacer protein sequence

<400> SEQUENCE: 22

Ser Ile Thr Ser Leu Tyr Lys Lys Ala Gly Ser
1               5                   10

<210> SEQ ID NO 23
<211> LENGTH: 7
<212> TYPE: PRT
<213> ORGANISM: Artificial Sequence
<220> FEATURE:
<223> OTHER INFORMATION: synthetic TEVrec protein sequence

<400> SEQUENCE: 23

Glu Asn Leu Tyr Phe Gln Phe
1               5

<210> SEQ ID NO 24
<211> LENGTH: 14
<212> TYPE: PRT
<213> ORGANISM: Artificial Sequence
<220> FEATURE:
<223> OTHER INFORMATION: synthetic Ndegron protein sequence

<400> SEQUENCE: 24

His Lys Ser Gly Ala Trp Lys Leu Pro Val Ser Leu Val Lys
1               5                   10

<210> SEQ ID NO 25
<211> LENGTH: 9
<212> TYPE: PRT
<213> ORGANISM: Artificial Sequence
<220> FEATURE:
<223> OTHER INFORMATION: synthetic spacer protein sequence

<400> SEQUENCE: 25

Arg Gly Ile Asp Lys Leu Asp Tyr Lys
1               5

<210> SEQ ID NO 26
<211> LENGTH: 48
<212> TYPE: PRT

<213> ORGANISM: Artificial Sequence
<220> FEATURE:
<223> OTHER INFORMATION: synthetic SF3b protein sequence

<400> SEQUENCE: 26

```
Glu Gln Leu Gln Ala Trp Arg Trp Glu Arg Glu Ile Asp Glu Arg Asn
1               5                   10                  15

Arg Pro Leu Ser Asp Glu Glu Leu Asp Ala Met Phe Pro Glu Gly Tyr
            20                  25                  30

Lys Val Leu Pro Pro Pro Ala Gly Tyr Val Pro Ile Arg Thr Pro Ala
        35                  40                  45
```

<210> SEQ ID NO 27
<211> LENGTH: 8
<212> TYPE: PRT
<213> ORGANISM: Artificial Sequence
<220> FEATURE:
<223> OTHER INFORMATION: synthetic spacer protein sequence

<400> SEQUENCE: 27

```
His Met Asp Arg Ile Pro Ala Val
1               5
```

<210> SEQ ID NO 28
<211> LENGTH: 242
<212> TYPE: PRT
<213> ORGANISM: Artificial Sequence
<220> FEATURE:
<223> OTHER INFORMATION: synthetic mKATE protein sequence

<400> SEQUENCE: 28

```
Ala Gly Ala Gly Ala Gly Ala Gly Ala Met Ser Glu Leu Ile Lys Glu
1               5                   10                  15

Asn Met His Met Lys Leu Tyr Met Glu Gly Thr Val Asn Asn His His
            20                  25                  30

Phe Lys Cys Thr Ser Glu Gly Glu Gly Lys Pro Tyr Glu Gly Thr Gln
        35                  40                  45

Thr Met Arg Ile Lys Val Val Glu Gly Gly Pro Leu Pro Phe Ala Phe
    50                  55                  60

Asp Ile Leu Ala Thr Ser Phe Met Tyr Gly Ser Lys Thr Phe Ile Asn
65                  70                  75                  80

His Thr Gln Gly Ile Pro Asp Phe Phe Lys Gln Ser Phe Pro Glu Gly
                85                  90                  95

Phe Thr Trp Glu Arg Val Thr Thr Tyr Glu Asp Gly Gly Val Leu Thr
            100                 105                 110

Ala Thr Gln Asp Thr Ser Leu Gln Asp Gly Cys Leu Ile Tyr Asn Val
        115                 120                 125

Lys Ile Arg Gly Val Asn Phe Pro Ser Asn Gly Pro Val Met Gln Lys
    130                 135                 140

Lys Thr Leu Gly Trp Glu Ala Ser Thr Glu Met Leu Tyr Pro Ala Asp
145                 150                 155                 160

Gly Gly Leu Glu Gly Arg Ser Asp Met Ala Leu Lys Leu Val Gly Gly
                165                 170                 175

Gly His Leu Ile Cys Asn Leu Lys Thr Thr Tyr Arg Ser Lys Lys Pro
            180                 185                 190

Ala Lys Asn Leu Lys Met Pro Gly Val Tyr Tyr Val Asp Arg Arg Leu
        195                 200                 205

Glu Arg Ile Lys Glu Ala Asp Lys Glu Thr Tyr Val Glu Gln His Glu
    210                 215                 220
```

```
Val Ala Val Ala Arg Tyr Cys Asp Leu Pro Ser Lys Leu Gly His Lys
225                 230                 235                 240

Gly Ser

<210> SEQ ID NO 29
<211> LENGTH: 1428
<212> TYPE: DNA
<213> ORGANISM: Artificial Sequence
<220> FEATURE:
<223> OTHER INFORMATION: synthetic tdTomato DNA sequence (Arabidopsis-
      optimized)

<400> SEQUENCE: 29
atggtgagca agggcgagga ggtcatcaaa gagttcatgc gcttcaaggt gcgcatggag       60
ggctccatga acggccacga gttcgagatc gagggcgagg cgagggccg ccctacgag       120 ggcacccaga ccgccaagct gaaggtgacc aagggcggcc cctgcccctt cgcctgggac     180
atcctgtccc cccagttcat gtacggctcc aaggcgtacg tgaagcaccc cgccgacatc     240
cccgattaca agaagctgtc cttccccgag ggcttcaagt gggagcgcgt gatgaacttc     300
gaggacggcg gtctggtgac cgtgacccag gactcctccc tgcaggacgg cacgctgatc     360
tacaaggtga agatgcgcgg caccaacttc ccccccgacg ccccgtaat gcagaagaag      420 accatgggct gggaggcctc caccgagcgc ctgtaccccc gcgacggcgt gctgaagggc     480
gagatccacc aggccctgaa gctgaaggac ggcggccact acctggtgga gttcaagacc     540
atctacatgg ccaagaagcc cgtgcaactg cccggctact actacgtgga caccaagctg     600
gacatcacct cccacaacga ggactacacc atcgtggaac agtacgagcg ctccgagggc     660
cgccaccacc tgttcctggg catggaccc ggcagcaccg gcagcggcag ctccggcacc      720
gcctcctccg aggacaacaa catggccgtc atcaaagagt tcatgcgctt caaggtgcgc     780
atggagggct ccatgaacgg ccacgagttc gagatcgagg cgagggcga gggccgcccc     840 tacgagggca cccagaccgc caagctgaag gtgaccaagg gcggcccct gcccttcgcc      900 tgggacatcc tgtcccccca gttcatgtac ggctccaagg cgtacgtgaa gcaccccgcc     960
gacatccccg attacaagaa gctgtccttc cccgagggct caagtggga gcgcgtgatg     1020 aacttcgagg acggcggtct ggtgaccgtg acccaggact cctccctgca ggacggcacg    1080
ctgatctaca aggtgaagat gcgcggcacc aacttccccc ccgacggccc cgtaatgcag    1140
aagaagacca tgggctggga ggcctccacc gagcgcctgt accccgcga cggcgtgctg     1200 aagggcgaga tccaccaggc cctgaagctg aaggacggcg ccactacct ggtggagttc     1260 aagaccatct acatggccaa gaagcccgtg caactgcccg gctactacta cgtggacacc    1320
aagctggaca tcacctccca caacgaggac tacaccatcg tggaacagta cgagcgctcc    1380
gagggccgcc accacctgtt cctgtacggc atggacgagc tgtacaag              1428

<210> SEQ ID NO 30
<211> LENGTH: 99
<212> TYPE: DNA
<213> ORGANISM: Artificial Sequence
<220> FEATURE:
<223> OTHER INFORMATION: synthetic spacer DNA sequence (Arabidopsis-
      optimized)

<400> SEQUENCE: 30
gccgctagtg cgatcgcatc agggagtggt tccggaagcg gctctggatc gggctcaggg       60
agtggttccg gcagcggctc tggatcggcg gccgctgca                             99
```

<210> SEQ ID NO 31
<211> LENGTH: 711
<212> TYPE: DNA
<213> ORGANISM: Artificial Sequence
<220> FEATURE:
<223> OTHER INFORMATION: syntheticTEV DNA sequence (Arabidopsis-
      optimized)

<400> SEQUENCE: 31

```
atgggagaaa gcttgtttaa ggggccgcgt gattacaacc cgatatcgag caccatttgt      60
catttgacga atgaatctga tgggcacaca acatcgttgt atggtattgg atttggtccc     120
ttcatcatta caaacaagca cttgtttaga agaaataatg aacactggt ggtccaatca      180 ctacatggtg tattcaaggt caagaacacc acgactttgc aacaacacct cattgatggg     240
agggacatga taattattcg catgcctaag gatttcccac catttcctca aaagctgaaa     300
tttagagagc acaaaggga agagcgcata tgtcttgtga caaccaactt ccaaactaag      360
agcatgtcta gcatggtgtc agacactagt tgcacattcc cttcaggaga tggcatattc     420
tggaagcatt ggattcaaac caaggatggg cagtgtggca gtccattagt atcaactaga     480
gatgggttca ttgttggtat acactcagca tcgaatttca ccaacacaaa caattatttc     540
acaagcgtgc cgaaaaactt catggaattg ttgacaaatc aggaggcgca gcagtgggtt     600
agtggttggc gattaaatgc tgactcagta ttgtgggggg ccataaaagt tttcatggtg     660
aaacctgaag agccttttca gccagttaag gaagcgactc aactcatgaa t              711
```

<210> SEQ ID NO 32
<211> LENGTH: 476
<212> TYPE: PRT
<213> ORGANISM: Artificial Sequence
<220> FEATURE:
<223> OTHER INFORMATION: synthetic tdTomato protein sequence
      (Arabidopsis-optimized)

<400> SEQUENCE: 32

```
Met Val Ser Lys Gly Glu Glu Val Ile Lys Glu Phe Met Arg Phe Lys
1               5                   10                  15

Val Arg Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Tyr Gly Ser Lys Ala Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Leu Val Thr Val Thr Gln Asp Ser
            100                 105                 110

Ser Leu Gln Asp Gly Thr Leu Ile Tyr Lys Val Lys Met Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175
```

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
            195                 200                 205

Tyr Thr Ile Val Glu Gln Tyr Glu Arg Ser Gly Arg His His Leu
210                 215                 220

Phe Leu Gly His Gly Thr Gly Ser Thr Gly Ser Gly Ser Ser Gly Thr
225                 230                 235                 240

Ala Ser Ser Glu Asp Asn Asn Met Ala Val Ile Lys Glu Phe Met Arg
                245                 250                 255

Phe Lys Val Arg Met Glu Gly Ser Met Asn Gly His Glu Phe Glu Ile
            260                 265                 270

Glu Gly Glu Gly Glu Gly Arg Pro Tyr Glu Gly Thr Gln Thr Ala Lys
            275                 280                 285

Leu Lys Val Thr Lys Gly Gly Pro Leu Pro Phe Ala Trp Asp Ile Leu
            290                 295                 300

Ser Pro Gln Phe Met Tyr Gly Ser Lys Ala Tyr Val Lys His Pro Ala
305                 310                 315                 320

Asp Ile Pro Asp Tyr Lys Lys Leu Ser Phe Pro Glu Gly Phe Lys Trp
                325                 330                 335

Glu Arg Val Met Asn Phe Glu Asp Gly Gly Leu Val Thr Val Thr Gln
            340                 345                 350

Asp Ser Ser Leu Gln Asp Gly Thr Leu Ile Tyr Lys Val Lys Met Arg
                355                 360                 365

Gly Thr Asn Phe Pro Pro Asp Gly Pro Val Met Gln Lys Lys Thr Met
            370                 375                 380

Gly Trp Glu Ala Ser Thr Glu Arg Leu Tyr Pro Arg Asp Gly Val Leu
385                 390                 395                 400

Lys Gly Glu Ile His Gln Ala Leu Lys Leu Lys Asp Gly Gly His Tyr
                405                 410                 415

Leu Val Glu Phe Lys Thr Ile Tyr Met Ala Lys Lys Pro Val Gln Leu
            420                 425                 430

Pro Gly Tyr Tyr Tyr Val Asp Thr Lys Leu Asp Ile Thr Ser His Asn
            435                 440                 445

Glu Asp Tyr Thr Ile Val Glu Gln Tyr Glu Arg Ser Glu Gly Arg His
450                 455                 460

His Leu Phe Leu Tyr Gly Met Asp Glu Leu Tyr Lys
465                 470                 475

<210> SEQ ID NO 33
<211> LENGTH: 33
<212> TYPE: PRT
<213> ORGANISM: Artificial Sequence
<220> FEATURE:
<223> OTHER INFORMATION: synthetic spacer protein sequence (Arabidopsis-
      optimized)

<400> SEQUENCE: 33

Ala Ala Ser Ala Ile Ala Ser Gly Ser Gly Ser Gly Ser Gly Ser Gly
1               5                   10                  15

Ser Gly Ser Gly Ser Gly Ser Gly Ser Gly Ser Ala Ala Ala
            20                  25                  30

Ala

<210> SEQ ID NO 34

```
<211> LENGTH: 237
<212> TYPE: PRT
<213> ORGANISM: Artificial Sequence
<220> FEATURE:
<223> OTHER INFORMATION: synthetic TEV protein sequence (Arabidopsis-
      optimized)

<400> SEQUENCE: 34
```

Met Gly Glu Ser Leu Phe Lys Gly Pro Arg Asp Tyr Asn Pro Ile Ser
1               5                   10                  15

Ser Thr Ile Cys His Leu Thr Asn Glu Ser Asp Gly His Thr Thr Ser
            20                  25                  30

Leu Tyr Gly Ile Gly Phe Gly Pro Phe Ile Ile Thr Asn Lys His Leu
        35                  40                  45

Phe Arg Arg Asn Asn Gly Thr Leu Val Val Gln Ser Leu His Gly Val
    50                  55                  60

Phe Lys Val Lys Asn Thr Thr Thr Leu Gln Gln His Leu Ile Asp Gly
65                  70                  75                  80

Arg Asp Met Ile Ile Ile Arg Met Pro Lys Asp Phe Pro Pro Phe Pro
                85                  90                  95

Gln Lys Leu Lys Phe Arg Glu Pro Gln Arg Glu Glu Arg Ile Cys Leu
            100                 105                 110

Val Thr Thr Asn Phe Gln Thr Lys Ser Met Ser Ser Met Val Ser Asp
        115                 120                 125

Thr Ser Cys Thr Phe Pro Ser Gly Asp Gly Ile Phe Trp Lys His Trp
    130                 135                 140

Ile Gln Thr Lys Asp Gly Gln Cys Gly Ser Pro Leu Val Ser Thr Arg
145                 150                 155                 160

Asp Gly Phe Ile Val Gly Ile His Ser Ala Ser Asn Phe Thr Asn Thr
                165                 170                 175

Asn Asn Tyr Phe Thr Ser Val Pro Lys Asn Phe Met Glu Leu Leu Thr
            180                 185                 190

Asn Gln Glu Ala Gln Gln Trp Val Ser Gly Trp Arg Leu Asn Ala Asp
        195                 200                 205

Ser Val Leu Trp Gly Gly His Lys Val Phe Met Val Lys Pro Glu Glu
    210                 215                 220

Pro Phe Gln Pro Val Lys Glu Ala Thr Gln Leu Met Asn
225                 230                 235

```
<210> SEQ ID NO 35
<211> LENGTH: 1728
<212> TYPE: DNA
<213> ORGANISM: Artificial Sequence
<220> FEATURE:
<223> OTHER INFORMATION: synthetic Degron DNA sequence for
      Arabidopsis:Citrine spacer TEVsite Ndeg spacer WUS

<400> SEQUENCE: 35
```

| | | | | | |
|---|---|---|---|---|---|
| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagtt | catctgcacc | accggcaagc | tgcccgtgcc | ctggcccacc | 180 |
| ctcgtgacca | ccttcggcta | cggcctgatg | tgcttcgccc | gctaccccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |

```
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaaggca    720
gcggccgctt cagggagtgg ttccggaagc gaaaacttgt acttccaatt ccacaagtct    780
ggtgcttgga agttgccagt ttctttggtt aaggggagtg gttccggcag cggctctgga    840
tcgtcaattg ctatggagcc gccacagcat cagcatcatc atcatcaagc cgaccaagaa    900
agcggcaaca acaacaacaa caagtccggc tctggtggtt acacgtgtcg ccagaccagc    960
acgaggtgga caccgacgac ggagcaaatc aaaatcctca agaactttta ctacaacaat   1020
gcaatccggt caccaacagc cgatcagatc cagaagatca ctgcaaggct gagacagttc   1080
ggaaagattg agggcaagaa cgtcttttac tggttccaga accataaggc tcgtgagcgt   1140
cagaagaaga gattcaacgg aacaaacatg accacaccat cttcatcacc caactcggtt   1200
atgatggcgg ctaacgatca ttatcatcct ctacttcacc atcatcacgg tgttcccatg   1260
cagagacctg ctaattccgt caacgttaaa cttaaccaag accatcatct ctatcatcat   1320
aacaagccat atcccagctt caataacggg aatttaaatc atgcaagctc aggtactgaa   1380
tgtggtgttg ttaatgcttc taatggctac atgagtagcc atgtctatgg atctatggaa   1440
caagactgtt ctatgaatta caacaacgta ggtggaggat gggcaaacat ggatcatcat   1500
tactcatctg caccttacaa cttcttcgat agagcaaagc ctctgtttgg tctagaaggt   1560
catcaagaag aagaagaatg tggtggcgat gcttatctgg aacatcgacg tacgcttcct   1620
ctcttcccta tgcacggtga agatcacatc aacggtggta gtggcgccat ctggaagtat   1680
ggccaatcgg aagttcgccc ttgcgcttct cttgagctac gtctgaac                1728
```

<210> SEQ ID NO 36
<211> LENGTH: 717
<212> TYPE: DNA
<213> ORGANISM: Artificial Sequence
<220> FEATURE:
<223> OTHER INFORMATION: synthetic Citrine DNA sequence

<400> SEQUENCE: 36

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga cccctgaagtt catctgcacc accggcaagc tgcccgtgcc ctggcccacc    180
ctcgtgacca ccttcggcta cggcctgatg tgcttcgccc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagct accagtccgc cctgagcaaa gaccccaacg agaagcgcga tcacatggtc    660
ctgctggagt tcgtgaccgc cgccgggatc actctcggca tggacgagct gtacaag       717
```

```
<210> SEQ ID NO 37
<211> LENGTH: 33
<212> TYPE: DNA
<213> ORGANISM: Artificial Sequence
<220> FEATURE:
<223> OTHER INFORMATION: synthetic spacer DNA sequence

<400> SEQUENCE: 37
gcagcggccg cttcagggag tggttccgga agc                           33

<210> SEQ ID NO 38
<211> LENGTH: 21
<212> TYPE: DNA
<213> ORGANISM: Artificial Sequence
<220> FEATURE:
<223> OTHER INFORMATION: synthetic TEVsite DNA sequence

<400> SEQUENCE: 38
gaaaacttgt acttccaatt c                                        21

<210> SEQ ID NO 39
<211> LENGTH: 42
<212> TYPE: DNA
<213> ORGANISM: Artificial Sequence
<220> FEATURE:
<223> OTHER INFORMATION: synthetic Ndeg DNA sequence

<400> SEQUENCE: 39
cacaagtctg gtgcttggaa gttgccagtt tctttggtta ag                 42

<210> SEQ ID NO 40
<211> LENGTH: 39
<212> TYPE: DNA
<213> ORGANISM: Artificial Sequence
<220> FEATURE:
<223> OTHER INFORMATION: synthetic spacer DNA sequence

<400> SEQUENCE: 40
gggagtggtt ccggcagcgg ctctggatcg tcaattgct                     39

<210> SEQ ID NO 41
<211> LENGTH: 876
<212> TYPE: DNA
<213> ORGANISM: Artificial Sequence
<220> FEATURE:
<223> OTHER INFORMATION: synthetic WUS DNA sequence

<400> SEQUENCE: 41
atggagccgc cacagcatca gcatcatcat catcaagccg accaagaaag cggcaacaac    60
aacaacaaca gtccggctc tggtggttac acgtgtcgcc agaccagcac gaggtggaca    120
ccgacgacgg agcaaatcaa atcctcaaa gaactttact acaacaatgc aatccggtca    180
ccaacagccg atcagatcca gaagatcact gcaaggctga cagttcgg aaagattgag     240 ggcaagaacg tctttttactg gttccagaac cataaggctc gtgagcgtca agaagagaga    300
ttcaacggaa caaacatgac cacaccatct tcatcaccca actcggttat gatggcggct    360
aacgatcatt atcatcctct acttcaccat catcacggtg ttcccatgca gagacctgct    420
aattccgtca acgttaaact taaccaagac catcatctct atcatcataa caagccatat    480
cccagcttca ataacgggaa tttaaatcat gcaagctcag gtactgaatg tggtgttgtt    540
aatgcttcta atggctacat gagtagccat gtctatggat ctatggaaca agactgttct    600
atgaattaca caacgtagg tggaggatgg gcaaacatgg atcatcatta ctcatctgca    660
```

```
ccttacaact tcttcgatag agcaaagcct ctgtttggtc tagaaggtca tcaagaagaa      720
gaagaatgtg gtggcgatgc ttatctggaa catcgacgta cgcttcctct cttccctatg      780
cacggtgaag atcacatcaa cggtggtagt ggcgccatct ggaagtatgg ccaatcggaa      840
gttcgccctt gcgcttctct tgagctacgt ctgaac                                876
```

<210> SEQ ID NO 42
<211> LENGTH: 576
<212> TYPE: PRT
<213> ORGANISM: Artificial Sequence
<220> FEATURE:
<223> OTHER INFORMATION: synthetic Degron protein sequence for
      Arabidopsis:Citrine spacer TEVsite Ndeg spacer WUS

<400> SEQUENCE: 42

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Gly Tyr Gly Leu Met Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ala
225                 230                 235                 240

Ala Ala Ala Ser Gly Ser Gly Ser Gly Ser Glu Asn Leu Tyr Phe Gln
                245                 250                 255

Phe His Lys Ser Gly Ala Trp Lys Leu Pro Val Ser Leu Val Lys Gly
            260                 265                 270

Ser Gly Ser Gly Ser Gly Ser Gly Ser Ser Ile Ala Met Glu Pro Pro
        275                 280                 285

Gln His Gln His His His His Gln Ala Asp Gln Glu Ser Gly Asn Asn
290                 295                 300

Asn Asn Asn Lys Ser Gly Ser Gly Gly Tyr Thr Cys Arg Gln Thr Ser
305                 310                 315                 320
```

Thr Arg Trp Thr Pro Thr Thr Glu Gln Ile Lys Ile Leu Lys Glu Leu
            325                 330                 335

Tyr Tyr Asn Asn Ala Ile Arg Ser Pro Thr Ala Asp Gln Ile Gln Lys
        340                 345                 350

Ile Thr Ala Arg Leu Arg Gln Phe Gly Lys Ile Glu Gly Lys Asn Val
            355                 360                 365

Phe Tyr Trp Phe Gln Asn His Lys Ala Arg Glu Arg Gln Lys Lys Arg
370                 375                 380

Phe Asn Gly Thr Asn Met Thr Thr Pro Ser Ser Pro Asn Ser Val
385                 390                 395                 400

Met Met Ala Ala Asn Asp His Tyr His Pro Leu Leu His His His His
                405                 410                 415

Gly Val Pro Met Gln Arg Pro Ala Asn Ser Val Asn Val Lys Leu Asn
            420                 425                 430

Gln Asp His His Leu Tyr His His Asn Lys Pro Tyr Pro Ser Phe Asn
        435                 440                 445

Asn Gly Asn Leu Asn His Ala Ser Ser Gly Thr Glu Cys Gly Val Val
    450                 455                 460

Asn Ala Ser Asn Gly Tyr Met Ser Ser His Val Tyr Gly Ser Met Glu
465                 470                 475                 480

Gln Asp Cys Ser Met Asn Tyr Asn Asn Val Gly Gly Trp Ala Asn
                485                 490                 495

Met Asp His His Tyr Ser Ser Ala Pro Tyr Asn Phe Phe Asp Arg Ala
                500                 505                 510

Lys Pro Leu Phe Gly Leu Glu Gly His Gln Glu Glu Glu Cys Gly
            515                 520                 525

Gly Asp Ala Tyr Leu Glu His Arg Arg Thr Leu Pro Leu Phe Pro Met
530                 535                 540

His Gly Glu Asp His Ile Asn Gly Gly Ser Gly Ala Ile Trp Lys Tyr
545                 550                 555                 560

Gly Gln Ser Glu Val Arg Pro Cys Ala Ser Leu Glu Leu Arg Leu Asn
                565                 570                 575

<210> SEQ ID NO 43
<211> LENGTH: 239
<212> TYPE: PRT
<213> ORGANISM: Artificial Sequence
<220> FEATURE:
<223> OTHER INFORMATION: synthetic Citrine protein sequence

<400> SEQUENCE: 43

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Gly Tyr Gly Leu Met Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

```
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 44
<211> LENGTH: 11
<212> TYPE: PRT
<213> ORGANISM: Artificial Sequence
<220> FEATURE:
<223> OTHER INFORMATION: synthetic spacer protein sequence

<400> SEQUENCE: 44

Ala Ala Ala Ala Ser Gly Ser Gly Ser Gly Ser
1               5                   10

<210> SEQ ID NO 45
<211> LENGTH: 7
<212> TYPE: PRT
<213> ORGANISM: Artificial Sequence
<220> FEATURE:
<223> OTHER INFORMATION: synthetic TEVsite protein sequence

<400> SEQUENCE: 45

Glu Asn Leu Tyr Phe Gln Phe
1               5

<210> SEQ ID NO 46
<211> LENGTH: 14
<212> TYPE: PRT
<213> ORGANISM: Artificial Sequence
<220> FEATURE:
<223> OTHER INFORMATION: synthetic Ndeg protein sequence

<400> SEQUENCE: 46

His Lys Ser Gly Ala Trp Lys Leu Pro Val Ser Leu Val Lys
1               5                   10

<210> SEQ ID NO 47
<211> LENGTH: 13
<212> TYPE: PRT
<213> ORGANISM: Artificial Sequence
<220> FEATURE:
<223> OTHER INFORMATION: synthetic spacer protein sequence

<400> SEQUENCE: 47

Gly Ser Gly Ser Gly Ser Gly Ser Gly Ser Ser Ile Ala
1               5                   10

<210> SEQ ID NO 48
<211> LENGTH: 292
```

```
<212> TYPE: PRT
<213> ORGANISM: Artificial Sequence
<220> FEATURE:
<223> OTHER INFORMATION: synthetic WUS protein sequence

<400> SEQUENCE: 48

Met Glu Pro Pro Gln His Gln His His His Gln Ala Asp Gln Glu
1               5                   10                  15

Ser Gly Asn Asn Asn Asn Lys Ser Gly Ser Gly Gly Tyr Thr Cys
                20                  25                  30

Arg Gln Thr Ser Thr Arg Trp Thr Pro Thr Thr Glu Gln Ile Lys Ile
            35                  40                  45

Leu Lys Glu Leu Tyr Tyr Asn Asn Ala Ile Arg Ser Pro Thr Ala Asp
50                  55                  60

Gln Ile Gln Lys Ile Thr Ala Arg Leu Arg Gln Phe Gly Lys Ile Glu
65                  70                  75                  80

Gly Lys Asn Val Phe Tyr Trp Phe Gln Asn His Lys Ala Arg Glu Arg
                85                  90                  95

Gln Lys Lys Arg Phe Asn Gly Thr Asn Met Thr Thr Pro Ser Ser Ser
                100                 105                 110

Pro Asn Ser Val Met Met Ala Ala Asn Asp His Tyr His Pro Leu Leu
                115                 120                 125

His His His His Gly Val Pro Met Gln Arg Pro Ala Asn Ser Val Asn
130                 135                 140

Val Lys Leu Asn Gln Asp His His Leu Tyr His His Asn Lys Pro Tyr
145                 150                 155                 160

Pro Ser Phe Asn Asn Gly Asn Leu Asn His Ala Ser Ser Gly Thr Glu
                165                 170                 175

Cys Gly Val Val Asn Ala Ser Asn Gly Tyr Met Ser Ser His Val Tyr
                180                 185                 190

Gly Ser Met Glu Gln Asp Cys Ser Met Asn Tyr Asn Asn Val Gly Gly
                195                 200                 205

Gly Trp Ala Asn Met Asp His His Tyr Ser Ser Ala Pro Tyr Asn Phe
210                 215                 220

Phe Asp Arg Ala Lys Pro Leu Phe Gly Leu Glu Gly His Gln Glu Glu
225                 230                 235                 240

Glu Glu Cys Gly Gly Asp Ala Tyr Leu Glu His Arg Arg Thr Leu Pro
                245                 250                 255

Leu Phe Pro Met His Gly Glu Asp His Ile Asn Gly Gly Ser Gly Ala
                260                 265                 270

Ile Trp Lys Tyr Gly Gln Ser Glu Val Arg Pro Cys Ala Ser Leu Glu
                275                 280                 285

Leu Arg Leu Asn
    290

<210> SEQ ID NO 49
<211> LENGTH: 2481
<212> TYPE: DNA
<213> ORGANISM: Artificial Sequence
<220> FEATURE:
<223> OTHER INFORMATION: synthetic CenH3 degron DNA sequence for
      Arabidopsis:Citrine spacer TEVsite Ndeg spacer CenH3 stop

<400> SEQUENCE: 49
atggtgagca aggcgagga gctgttcacc ggggtggtgc ccatcctggt cgagctggac    60
ggcgacgtaa acggccacaa gttcagcgtg tccggcgagg gcgagggcga tgccacctac   120
```

```
ggcaagctga ccctgaagtt catctgcacc accggcaagc tgcccgtgcc ctggcccacc        180
ctcgtgacca ccttcggcta cggcctgatg tgcttcgccc gctacccgca ccacatgaag        240
cagcacgact tcttcaagtc cgccatgccc gaaggctacg tccaggagcg caccatcttc        300
ttcaaggacg acggcaacta caagacccgc gccgaggtga agttcgaggg cgacaccctg        360
gtgaaccgca tcgagctgaa gggcatcgac ttcaaggagg acggcaacat cctggggcac        420
aagctggagt acaactacaa cagccacaac gtctatatca tggccgacaa gcagaagaac        480
ggcatcaagg tgaacttcaa gatccgccac aacatcgagg acggcagcgt gcagctcgcc        540
gaccactacc agcagaacac ccccatcggc gacggccccg tgctgctgcc cgacaaccac        600
tacctgagct accagtccgc cctgagcaaa gaccccaacg agaagcgcga tcacatggtc        660
ctgctggagt tcgtgaccgc cgccgggatc actctcggca tggacgagct gtacaaggca        720
gcggccgctt cagggagtgg ttccggaagc gaaaacttgt acttccaatt ccacaagtct        780
ggtgcttgga agttgccagt ttctttggtt aaggggagtg gttccggcag cggctctgga        840
tcgtcaattg ctatggcgag aaccaagcat cgcgttacca ggtcacaacc tcggaatcaa        900
actggtatct aaatctgct ttctctttca attttactt ctgattttac ccagaatttt         960
aggtttttta tttcgatttt gttaaccota gatttcgaat ctgaaatttg tagatgccgc       1020
cggtgcttca tcttctcagg cggcaggtcc aactacggta cggcatcttt ttccgtctta       1080
gggtttccaa tgtttcttcc ttttatcgtt atgatcaaat ttgtttatct atcgaaattg       1140
aagaccccga caaggagagg cggtgaaggt ggagataata ctcaacaaag tgagtttttt       1200
atatttgaag tctttttttt ccctcttttc atctcttttg tttgtgaagt tattcttttg       1260
taacatctgc agcaaatcct acaacttcac cagctactgg tacaagggta agattttttgt      1320 gaccattgct tatgaactgc ttcaactttg atttcgttat taagctgaca aaattctcgt       1380
tttggtttgt caagagaggg gctaagagat ccagacaggc tatgccacga ggtttgtttt       1440
aaaaaaaaaa ccaatctctt gtgatatccc tgagaataca ggacacttag tgtgtttaaa       1500
actaatcttc ggtgttgtcc ttgtaggctc acagaagaag tcttatcgat acaggccagg       1560
aaccgttgct ctaaaagaga ttcgccattt ccagaagcag acaaaccttc ttattccggc       1620
tgccagtttc ataagagaag ttagttactc tttttcttac cagccataat aagtttcaca       1680
gcttaacaat attcatatat actaacagag gcacaagcct tttggtgttt aatgtggcta       1740
gttttaggat ttgcacaccc cacacatatc tgagcatcaa tgcagtgtac atagtgagtg       1800
atatagcaat ttaactaaaa ttcagagtaa tcgtgaggcc aaccctcctt gtttaaggag       1860
tgtgtaatct agtttgtctt tgaggttatg agctcataga ttcagaacca tatgattcct       1920
gtagctacaa aactcaacat gaatcgtcag tgatgtggaa atgctgattt gtgttacaaa       1980
caaactattt tacattgttt ttccaggtga gaagtataac ccatatgttg gcccctcccc       2040
aaatcaatcg ttggacagct gaagctcttg ttgctcttca agaggtacca atccttcaac       2100 tttttctttta tacgaatgta tgaatataga tatagagata gtcacacatt tcaactaatg       2160
tcattcccct tgatgaccaa tcaacctaat cacacaaatt ctttgtggta ggcggcagaa       2220
gattacttgg ttggtttgtt ctcagattca atgctctgtg ctatccatgc aagacgtgtt       2280
actctaagta agtactctaa aagaagacat ttttcagtct caacttagga atcacaagca       2340 tacatttttat atccctttga atcattagtt acttgaatat catatataaa aatgcttatc       2400
tatatctgtt ttttgttcat atcagtgaga aaagactttg aacttgcacg ccggcttgga       2460
ggaaaaggca gaccatggtg a                                                  2481
```

<210> SEQ ID NO 50
<211> LENGTH: 717
<212> TYPE: DNA
<213> ORGANISM: Artificial Sequence
<220> FEATURE:
<223> OTHER INFORMATION: synthetic Citrine DNA sequence (CenH3
      depletion)

<400> SEQUENCE: 50

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccttcggcta cggcctgatg tgcttcgccc gctacccega ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggag acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagct accagtccgc cctgagcaaa gaccccaacg agaagcgcga tcacatggtc   660
ctgctggagt tcgtgaccgc cgccgggatc actctcggca tggacgagct gtacaag      717
```

<210> SEQ ID NO 51
<211> LENGTH: 33
<212> TYPE: DNA
<213> ORGANISM: Artificial Sequence
<220> FEATURE:
<223> OTHER INFORMATION: synthetic spacer DNA sequence (CenH3 depletion)

<400> SEQUENCE: 51

```
gcagcggccg cttcagggag tggttccgga agc                                33
```

<210> SEQ ID NO 52
<211> LENGTH: 21
<212> TYPE: DNA
<213> ORGANISM: Artificial Sequence
<220> FEATURE:
<223> OTHER INFORMATION: synthetic TEVsite DNA sequence (CenH3
      depletion)

<400> SEQUENCE: 52

```
gaaaacttgt acttccaatt c                                             21
```

<210> SEQ ID NO 53
<211> LENGTH: 42
<212> TYPE: DNA
<213> ORGANISM: Artificial Sequence
<220> FEATURE:
<223> OTHER INFORMATION: synthetic Ndeg DNA sequence (CenH3 depletion)

<400> SEQUENCE: 53

```
cacaagtctg gtgcttggaa gttgccagtt tctttggtta ag                      42
```

<210> SEQ ID NO 54
<211> LENGTH: 39
<212> TYPE: DNA
<213> ORGANISM: Artificial Sequence
<220> FEATURE:

-continued

<223> OTHER INFORMATION: synthetic spacer DNA sequence (CenH3 depletion)

<400> SEQUENCE: 54

```
gggagtggtt ccggcagcgg ctctggatcg tcaattgct                              39
```

<210> SEQ ID NO 55
<211> LENGTH: 1626
<212> TYPE: DNA
<213> ORGANISM: Artificial Sequence
<220> FEATURE:
<223> OTHER INFORMATION: synthetic CenH3 DNA sequence (CenH3 depletion)

<400> SEQUENCE: 55

```
atggcgagaa ccaagcatcg cgttaccagg tcacaacctc ggaatcaaac tggtatctta      60
aatctgcttt ctctttcaat ttttacttct gattttaccc agaattttag gttttttatt     120
tcgattttgt taaccctaga tttcgaatct gaaatttgta gatgccgccg gtgcttcatc     180
ttctcaggcg gcaggtccaa ctacggtacg gcatcttttt ccgtcttagg gtttccaatg     240
tttcttcctt ttatcgttat gatcaaattt gtttatctat cgaaattgaa gaccccgaca     300
aggagaggcg gtgaaggtgg agataatact caacaaagtg agtttttat atttgaagtc      360
ttttttttcc ctctttcat ctctttgtt tgtgaagtta ttcttttgta acatctgcag       420
caaatcctac aacttcacca gctactggta caagggtaag attttgtga ccattgctta     480
tgaactgctt caactttgat ttcgttatta agctgacaaa attctcgttt ggtttgtca     540
agagagggc taagagatcc agacaggcta tgccacgagg tttgttttaa aaaaaaaacc     600
aatctcttgt gatatccctg agaatacagg acacttagtg tgtttaaaac taatcttcgg    660
tgttgtcctt gtaggctcac agaagaagtc ttatcgatac aggccaggaa ccgttgctct    720
aaaagagatt cgccatttcc agaagcagac aaaccttctt attccggctg ccagtttcat    780
aagagaagtt agttactctt tttcttacca gccataataa gtttcacagc ttaacaatat    840
tcatatatac taacagaggc acaagccttt tggtgtttaa tgtggctagt tttaggattt    900
gcacacccca cacatatctg agcatcaatg cagtgtacat agtgagtgat atagcaattt    960
aactaaaatt cagagtaatc gtgaggccaa ccctccttgt ttaaggagtg tgtaatctag   1020
tttgtctttg aggttatgag ctcatagatt cagaaccata tgattcctgt agctacaaaa   1080
ctcaacatga atcgtcagtg atgtggaaat gctgatttgt gttacaaaca aactatttta   1140
cattgttttt ccaggtgaga agtataaccc atatgttggc ccctccccaa atcaatcgtt   1200
ggacagctga agctcttgtt gctcttcaag aggtaccaat ccttcaactt tttctttata   1260
cgaatgtatg aatatagata tagagatagt cacacatttc aactaatgtc attccccttg   1320
atgaccaatc aacctaatca cacaaattct ttgtggtagg cggcagaaga ttacttggtt   1380
ggtttgttct cagattcaat gctctgtgct atccatgcaa gacgtgttac tctaagtaag   1440
tactctaaaa gaagacattt ttcagtctca acttaggaat cacaagcata cattttatat   1500
ccctttgaat cattagttac ttgaatatca tatataaaaa tgcttatcta tatctgtttt   1560
ttgttcatat cagtgagaaa agactttgaa cttgcacgcc ggcttggagg aaaaggcaga   1620
ccatgg                                                              1626
```